(12) United States Patent
Embry

(10) Patent No.: US 8,184,276 B2
(45) Date of Patent: May 22, 2012

(54) CONTINUOUS INDEX OF REFRACTION COMPENSATION METHOD FOR MEASUREMENTS IN A MEDIUM

(76) Inventor: Carl Embry, Boulder, CO (US)

( * ) Notice: Subject to any disclaimer, the term of this patent is extended or adjusted under 35 U.S.C. 154(b) by 284 days.

(21) Appl. No.: 12/632,102

(22) Filed: Dec. 7, 2009

(65) Prior Publication Data

US 2010/0141928 A1   Jun. 10, 2010

Related U.S. Application Data

(60) Provisional application No. 61/120,662, filed on Dec. 8, 2008.

(51) Int. Cl.
*G01N 21/41* (2006.01)
(52) U.S. Cl. ............ 356/128; 356/130; 356/243.1
(58) Field of Classification Search .......... 356/128–138, 356/243.1–243.8
See application file for complete search history.

(56) References Cited

U.S. PATENT DOCUMENTS

| | | | |
|---|---|---|---|
| 3,680,963 A | 8/1972 | Edwards et al. | |
| 4,640,615 A | 2/1987 | Sasaki | |
| 4,964,721 A | 10/1990 | Ulich et al. | |
| 5,231,401 A | 7/1993 | Kaman et al. | |
| 5,309,288 A | 5/1994 | Kahre | |
| 5,343,284 A | 8/1994 | Keeler et al. | |
| 5,446,529 A | 8/1995 | Stettner et al. | |
| 5,457,639 A | 10/1995 | Ulich et al. | |
| 5,565,978 A | 10/1996 | Okubo et al. | |
| 5,617,201 A | 4/1997 | K.ang.hre | |
| 5,696,577 A | 12/1997 | Stettner et al. | |
| 6,133,989 A | 10/2000 | Stettner et al. | |
| 6,414,746 B1 | 7/2002 | Stettner et al. | |
| 6,549,276 B1 * | 4/2003 | Longtin | 356/128 |
| 6,963,354 B1 | 11/2005 | Scheps | |
| 7,030,976 B2 | 4/2006 | Hosseinioun | |
| 2008/0273248 A1 * | 11/2008 | Beder et al. | 359/665 |
| 2009/0002690 A1 * | 1/2009 | Glimm | 356/139.1 |
| 2010/0085560 A1 * | 4/2010 | Fedele et al. | 356/134 |

OTHER PUBLICATIONS

Austin et al. (1976) "The Index of Refraction of Seawater," SIO Ref 76-1 Scripps Institution of Oceanography, La Jolla, CA.

* cited by examiner

*Primary Examiner* — Hoa Pham
(74) *Attorney, Agent, or Firm* — Greenlee Sullivan P.C.

(57) ABSTRACT

Described herein are devices and methods for making extremely accurate measurements in a medium by continuously measuring the index of refraction of the medium such as water or biological tissue. Also described herein is a device for constantly measuring the index of refraction, and using the index of refraction data to constantly calibrate the optical measurement device. In addition, a primary measurement device (a ladar) that is optimized for data collection in a volume backscattering medium such as water or biological tissue is described, along with data results from the lab.

15 Claims, 22 Drawing Sheets

CONTINUOUS INDEX OF REFRACTION COMPENSATION METHOD FOR MEASUREMENTS IN A MEDIUM

CROSS REFERENCE TO RELATED APPLICATION

This application claims the benefit of and priority under 35 U.S.C. §119(e) to U.S. Provisional Application 61/120,662 filed on Dec. 8, 2008, which is herein incorporated by reference in its entirety.

BACKGROUND OF THE INVENTION

This invention is in the field of optical measurements and imaging. This invention relates to methods for making extremely accurate measurements in a medium by continuously measuring the index of refraction of the medium, such as water or biological tissue.

The index of refraction of a medium is the ratio of the speed of light in a vacuum to the speed of light in the medium. This is an important parameter, as the index of refraction not only changes the time it takes for the light to travel through the medium, but also can change the angle of propagation. This is highly important when making very precise optical measurements in a medium that has a variable index of refraction. For instance, when taking a 3D laser scan of a scene at the bottom of the ocean, the correct index at that depth and temperature are needed in order to measure range and angle accurately and thus create a dimensionally correct 3D image.

Austin and Halikas [R. W. Austin and G. Halikas, "The index of refraction of seawater", SIO Ref 76-1 (Scripps Institution of Oceanography, La Jolla, Calif., 1976)] presented extensive tables and interpolation algorithms for the index of refraction of seawater as a function of wavelength of light, salinity, temperature, and pressure. The index of refraction of seawater varied from 1.329128 to 1.366885. In addition, suspended particulate matter in sea water changes the index of refraction. Living phytoplankton typically have indices of refraction in the range of 1.01 to 1.09 relative to the index of refraction of seawater. Detritus and inorganic particles generally have indices in the range of 1.15 to 1.2 relative to seawater.

When using light to measure distance in a medium, the time it takes for the signal to reach the target and return is measured and then used to calculate distance. The simple equation is $$R = cT/2n \quad (1)$$

where R=range to target, c=speed of light in a vacuum, n is the index of refraction of the medium, and T is the measured time for the signal to travel to the target and back.

One method is to arbitrarily choose the index to be the average of the 2 extreme values stated above (1.348) when calculating range using equation 1. Now assume the actual index is 1.329128 and the distance to the target is 10 m. If range is calculated using the average index (1.348), the range is computed as 9.86 m, a 14 cm (~5") error. The methods and devices describe herein eliminate this error by constantly measuring the index of refraction and using the updated index in the primary measurement device.

In addition to range errors, a varying index will also cause angle errors. When light passes from one medium (air in the instrument housing) to the medium (ocean water) the light refracts by Snell's law:

$$n_1 \sin\theta_1 = n_2 \sin\theta_2 \quad (2)$$

where $n_1$ is the index of the medium in the housing, $\theta_1$ is the angle of incidence (compared to normal) of the beam as it passed from $n_1$ to $n_2$, $n_2$ is the index of the medium, and $\theta_2$ is the angle of the beam (compared to normal) as it propagates through the medium.

In a scanning system this equates to spatial offsets. In triangulation, stereoscopic vision, photometric stereo, photoclinometry, stereo-photoclinometry, and other angular based measurement systems this equates to angle and range offsets. For instance, a beam with a 15° angle from normal exiting an optical instrument and travelling 10 m in water (index=1.348) will produce a spot 1.96 m from normal at the 10 m range. In comparison, a beam with a 15° angle from normal exiting an optical instrument and travelling 10 m in different seawater (index=1.366885) will produce a spot 1.93 m from normal at the 10 m range—an error of greater than 1 inch. The methods and devices described herein eliminate these errors.

The current underwater 3D inspection technology is sonar. This technology is used for oil and water pipeline inspection, underwater construction, bridge inspection, hydroelectric dam inspection, and tunnel inspection. However surveyors currently need higher resolution 3D imaging to perform several underwater tasks and sonar cannot reach the higher resolutions.

Several papers and patents discuss underwater laser scanning, laser triangulation, and photometric stereo systems to provide high resolution 3D data. Most of these papers and patents show lower resolution data, or high resolution data in a lab environment. When making real world measurements working at various depths in various oceans, the index of refraction will vary by up to 3% causing errors as shown above. None of this prior art discusses the effects of index of refraction variation on the resolution of the system, much less how to correct for it.

SUMMARY OF THE INVENTION

The methods and devices described herein provide continuous measurement of the index of refraction of a medium, and utilize that measured index to calibrate the primary remote measurements in the medium. By having an accurate index of refraction measurement in real time, the measurement errors described in the background can be avoided. This measurement is necessary for accurate underwater measurements in an uncontrolled environment that is not mentioned in the prior art.

In one aspect, provided herein are methods for making single or continuous index of refraction measurements of a medium. Useful media include both fresh and salt water. A method of this aspect comprises the steps of: passing a beam of energy from a first medium into a second medium; determining a parameter of the beam of energy associated with the beam passing from the first medium into the second medium; and relating the parameter of the beam of energy to the index of refraction of the second medium. In embodiments, the beam of energy is a beam of electromagnetic energy, such as a laser beam, or a beam of acoustic energy.

Useful parameters of the beam of energy include: an angular deflection of the beam, a spatial deflection of the beam over a known distance, a speed of the beam, a phase of the beam, a time required for the beam to traverse a known distance, a total internal reflection (TIR) angle for transmission of the beam from the first medium into the second medium, an intensity change of the beam after TIR and any combination of these. In a specific embodiment, the parameter of the beam is determined by monitoring the beam using an array detector, such as a one- or two-dimensional array detector, a camera, or any combination of these.

In one embodiment, the determining step includes measuring a deflection of the beam by measuring a first deflection of the beam when the second medium is a reference medium and measuring a second deflection of the beam when the second medium is the medium for which the index of refraction is to be measured. In an embodiment, the determining step includes measuring a time required for the beam to traverse a known distance by measuring a first time required for the beam to traverse a known distance in the second medium when the second medium is a reference medium and measuring a second time required for the beam to traverse a known distance in the second medium when the second medium is the medium for which the index of refraction is to be measured. In an embodiment, the determining step includes measuring a total internal reflection angle for transmission of the beam from the first medium into the second medium by measuring a first total internal reflection angle for transmission of the beam from the first medium into the second medium when the second medium is a reference medium and measuring a second total internal reflection angle for transmission of the beam from the first medium into the second medium when the second medium is the medium for which the index of refraction is to be measured. In an embodiment, the determining step further includes determining an intensity change of the beam upon TIR.

For certain embodiments, the first medium is a window, for example comprising a material including glass, plastic, crystal, polymer, and any combination of these. In another embodiment, the first medium comprises a gas, for example air or dry nitrogen. In specific embodiments, the second medium is the medium for which the index of refraction is to be measured, for example the second medium comprises water.

Another method of this aspect for making an index of refraction measurement of a medium comprises the steps of: measuring a physical parameter of the medium; and relating the physical parameter of the medium to the index of refraction of the medium. Useful physical parameters include: the temperature of the medium, the pressure of the medium, the pH of the medium, the salinity of the medium and any combination of these. In an embodiment, the index of refraction of the medium is determined for a wavelength which matches a wavelength utilized by a primary measurement sensor In an embodiment, the relating step includes using a mathematical model for determining the index of refraction of the medium from the measured physical parameter of the medium, for example where the mathematical model is an analytic function. In particular embodiments, the relating step includes determining the index of refraction of the medium using a look-up table, for example a look-up table including values of the index of refraction of the medium for a range of values of the physical parameter of the medium. In a specific embodiment, the relating step includes determining the index of refraction of the medium by interpolating between values in the look-up table. In one embodiment, a useful analytic function is a function of wavelength or the look-up table includes values of the index of refraction of the medium for a range of wavelength values.

In another aspect, provided herein are methods for correcting range, angle, and/or imaging measurements in a medium. A method of this aspect comprises the steps of: making a range, angle, or imaging measurement in a medium; measuring the index of refraction of the medium; and correcting the range, angle, or imaging measurement for errors associated with use of a second index of refraction different from the measured index of refraction of the medium. In embodiments, the index of refraction of the medium is measured using a method as described above.

In a specific embodiment, the second index of refraction is an approximate index of refraction of the medium. In an embodiment, the second index of refraction is the index of refraction of a vacuum. In an embodiment, the second index of refraction is the index of refraction of a reference medium.

In another aspect, provided herein are methods for making range, angle, or imaging measurements in a medium. A method of this aspect comprises the steps of: measuring the index of refraction of the medium; and making a range, angle, or imaging measurement utilizing the measured index of refraction of the medium. Useful index of refraction of the medium measurements include those measured using the methods described above.

Useful range or imaging measurements include: laser scanning, ladar, flash ladar, laser triangulation, photometric stereo, stereoscopic vision, structured light, photoclinometry, stereo-photoclinometry, holographic systems, AMCW phase detection, chirped AMCW, amplitude FMCW, true FMCW, time of flight pulse detection, pulse modulation codes and any combination of these.

In embodiments, a device useful for making a range, angle, or imaging measurement comprises elements including: scanning systems, a multi-detector system or camera (2D or 3D) where each detector pixel equates to an angle, and any combination of these. Useful range, angle, imaging, and index of refraction measurements include those made at locations within 20 meters of one another within the medium.

Useful range, angle, or imaging measurements include electromagnetic energy and acoustic energy based measurement. For example, in one embodiment, an electromagnetic energy based range, angle, or imaging measurement utilizes electromagnetic energy having a wavelength selected over the range of 300 to 900 nm. Optionally, the measurement of the index of refraction of the medium is made at the wavelength of the electromagnetic or acoustic energy.

In another aspect, provided herein are devices for making single or continuous index of refraction measurements of a medium. A specific device of this aspect comprises: a housing; a window in the housing; a source for generating a beam of energy, wherein at least a portion of the beam of energy is directed into a medium through the window; a detector for detecting the beam of energy; and electronics for determining a parameter of the beam associated with the beam passing from the window into the medium; and wherein the source, the detector and the electronics are positioned within an interior of the housing, the housing configured for preventing the medium from penetrating into the interior of the housing. Optionally, a device of this aspect further comprises a target positioned within the medium at a known distance from the window. Useful targets include reflective optics, dispersive optics, and mirrors.

In a specific embodiment, the detector comprises an array detector, for example a one- or two-dimensional array detector and or a camera. In an embodiment, the housing is filled with a second medium comprising a gas, for example air or dry nitrogen. In embodiments, the index of refraction measurement device determines the index of refraction of the medium using a method described above.

In another embodiment, a device for making range, angle, or imaging measurements in a medium comprises: a means for measuring the index of refraction of the medium; and a means for making range, angle, or imaging measurements in the medium utilizing a measured index of refraction of the medium. Useful index of refraction measuring means include those described above and those which determine the index of refraction of the medium using the methods described above. Useful range or imaging measurement means include those described above.

In another aspect, describe herein are monostatic ladar devices. A specific device of this aspect comprises: a collimated or nearly collimated light source generating light directed into a medium; a detector and associated electronics positioned to detect at least a portion of the light which is scattered or reflected from the medium or an object in the medium; and an obscuration means for preventing at least a portion of the scattered or reflected light from reaching the detector. In an embodiment, the obscuration means reduces the dynamic range of the detector and electronics and reduces volume backscatter from a medium at a first range, for example a first range less than 3 meters. In an embodiment, the collimated light source is a laser. In an embodiment, a monostatic ladar device further comprises an aperture through which the light is directed, for example an aperture having a diameter of 0.5 mm to 1.0 cm.

Optionally, a monostatic ladar device further comprises a receiving optic for directing the scattered or reflected light to the detector. In one embodiment, an obscuration means comprises a hole in a receiving optic. In an embodiment, the receiving optic is positioned to direct at least a portion of the scattered or reflected light to the detector. In an embodiment, the obscuration is a central obscuration. In an embodiment, the obscuration means comprises an actual obscuration physically blocking at least a portion of the scattered or reflected light from reaching the detector, for example the actual obscuration comprises a secondary mirror.

In a specific embodiment, the collimated light source is a laser, the obscuration is a central hole in a receive mirror, the laser beam transmits through the hole in the receive mirror to illuminate the target in the medium, and a scanning device is used after the receive mirror to direct the transmit beam and receiver field-of-view.

Further embodiments are described below:

Coupled Index Measurement with Primary Sensor. This embodiment comprises a method and/or device for measuring the index of refraction of the medium, and sending those measurements to the primary sensor. The primary sensor then uses that index measurement to obtain highly accurate measurements in the medium. The primary sensor could be any sensor such as a 3D laser scanner, flash ladar, triangulation sensor (laser or non-laser), stereoscopic vision system, photometric stereo vision system, photoclinometry system, stereo-photoclinometry system, or other optical measurement device to obtain highly accurate 3D data. This index correction is generally needed for making underwater measurements with accuracies better than a few inches.

Index Measurement—Centroid. There are several methods and devices for making the continuous real-time index measurements. One embodiment for making index measurements comprises a small, self contained underwater housing. The light source, detector, and electronics are all housed in one part of the container and view the outside environment through a window. This is called the primary part of the container. A diffuse plate that is in integral part of the housing is located a distance (10 cm for example) from the window. This is called the target portion of the container. A light source located in the primary part of the container illuminates the target portion of the container. The 10 cm distance from the primary window to the target is open and therefore filled with the medium of propagation. Therefore the light is propagating through this medium.

The light source is rigidly positioned at an angle, so the light meets the surface of the target at an angle, such as 45°. The light creates a diffuse spot on the target. A camera located in the primary housing is used to image the illuminated spot on the diffuse target. A camera refers to any detector (2D or 1D) capable of imaging the diffuse target. A filter is used in front of the detector to suppress any background light that is not of the wavelength of interest.

An important aspect is that the image of the illuminated spot covers thousands to tens of thousands of detector elements. The image of the illuminated spot is analyzed in signal processing software to calculate the centroid of the spot. By having the spot imaged on a large number of pixels, sub-pixel resolution is achieved for the centroid. It is this sub-pixel resolution that allows for very precise measurement of the index of refraction.

This measured centroid is compared to the centroid location measured during factory calibration in air. The difference in spot location from the air measurement to the measurement in the medium is used to calculate the index of refraction.

Averaging of hundreds or thousands of images within 1 minute can reduce individual image errors or temporary disturbances (particulates, etc). Additional intelligence can be included that discard outliers, as the index should not change by a large percentage quickly (temperature, pressure, and salinity will change on the order of a few seconds, not subsecond). The exact algorithm for calculating the centroid is not described herein, as there are numerous algorithms for centroid detection, such as highest intensity, quadratic curve fitting, two-dimensional quadratic interpolation, illumination center, modified illumination center, and least-squares methods such as principal component or eigenvector fits. Any of these algorithms could be applied herein with the same intent and purpose.

In another embodiment, the target plate is shiny (like a mirror) and reflects the beam back onto the primary housing. This beam directly illuminates the detector (camera). The centroid is then calculated as in the primary embodiment. The mirror could be metal, dielectric, or other material. The mirror could be exposed directly to the medium, or reside behind a protective window.

In another embodiment, the target plate is shiny (like a mirror) and reflects the beam back onto the primary housing. A diffuse window is placed in front of the detector (camera). The camera images this diffuse image of the beam. The centroid is then calculated as in the primary embodiment. The target mirror could be metal, dielectric, or other material. The mirror could be exposed directly to the medium, or reside behind a protective window.

The light source should be transparent for the medium of interest. For water, this is primarily in the visible spectrum, while for blood this would be red or near-infrared. The light source could be a laser, LED, OLED, collected incandescent bulb with a colored glass for wavelength selection, or any other directional or non-directional source. The light source can be CW or pulsed. Pulsed has the advantage of freezing time, whereas CW has the advantage of spatial averaging over a longer integration period. CW light sources are generally cheaper (for lasers), whereas pulsed sources use less power (for LEDs). The example wavelengths of radiation used here are visible and infrared, however any wavelength of electromagnetic or acoustic energy are considered part of this disclosure.

The detector needs to be able to detect the wavelength of interest. For green/blue/red this would be silicon, but could be any other detector sensitive to visible light. For the infrared this would most likely be InGaAs, but could be any other detector sensitive to infrared light.

The preferred detector format is a 2D array such as a camera, however a 1D array could also be used.

Index Measurement—Holographic. Another embodiment comprises a holographic based measurement technique. A device embodiment of this aspect comprises a small, self contained underwater housing. The light source, detector, and electronics are all housed in one part of the container and view the outside environment through a window. This is called the primary part of the container. A shiny plate that is an integral part of the housing is located a short distance (1 cm for example) from the window. This is called the target portion of the container. A coherent light source located in the primary part of the container illuminates the target portion of the container. The 1 cm distance from the primary window to the target is open and therefore filled with the medium of propagation. Therefore the light is propagating through the medium.

The coherent light source is rigidly positioned at an angle, so the light meets the surface of the target at an angle, such as 45°. Since the target plate is shiny (like a mirror) it reflects the beam back onto the primary housing. The mirror could be metal, dielectric, or other material. This beam directly illuminates the detector (camera).

A portion of the outgoing beam is used as a local oscillator to also illuminate the camera. The interference of this local oscillator with the return beam produces an interference pattern on the camera. The spatial frequency of this interference pattern is directly related to the angular difference of the two beams. By measuring this spatial frequency on the camera image, the angle between the two beams can be measured with immense accuracy.

This angle is compared to the angle measured during calibration at the factory in air. The difference in angle from the air measurement to the measurement in the medium can be used to calculate the index of refraction.

A camera refers to any detector capable of imaging the diffuse target, 2D or 1D. A filter is used in front of the detector to suppress any background light that is not of the wavelength of interest.

Averaging of hundreds or thousands of images within a few seconds can reduce individual image errors or temporary disturbances (particulates, etc). Additional intelligence can be included that discard outliers, as the index should not change by a large percentage quickly (temperature, pressure, and salinity will change on the order of several seconds, not sub-second). The exact algorithm for calculating the spatial frequency of the interference pattern is not described herein, as there are numerous algorithms for frequency calculation, such as counting zero crossings, phase unwrapping, or Fourier transforms. Any of these algorithms could be applied herein with the same intent and purpose.

Since holography allows for extremely accurate measurement of angle, the propagation distance does not have to be as large. Therefore this method may be better suited for biological sensing where the sensor may have to be inserted in living tissue or bloodstreams.

The light source should be transparent for the medium of interest. For water, this is primarily the visible spectrum, while for blood this would be red or near-infrared. The light source for holography must be at least partially coherent which makes a laser the preferred source, however any partially coherent source could be used. The light source can be CW or pulsed. Pulsed has the advantage of freezing time, whereas CW has the advantage of spatial averaging over a longer integration period. CW light sources are generally cheaper (lasers), whereas pulsed sources use less power (diodes). The example wavelengths of radiation used here are visible and infrared, however any wavelength of electromagnetic or acoustic energy are considered part of this disclosure.

The detector needs to be able to detect the wavelength of interest. For green/blue/red this would be silicon, but could be any other detector sensitive to visible light. For the infrared this would most likely be InGaAs, but could be any other detector sensitive to infrared light.

The preferred detector format is a 2D array such as a camera, however a 1D array could also be used.

Index Measurement—Time. Another embodiment comprises a time based measurement technique. A device embodiment of this aspect comprises a small, self contained underwater housing. The light source, detector, and electronics are all housed in one part of the container and view the outside environment through a window. This is called the primary part of the container. A shiny plate that is in integral part of the housing is located a distance (for instance 10 cm) from the window. This is called the target portion of the container. A light source located in the primary part of the container sends a pulse of light to the target portion of the container. The 10 cm distance from the primary window to the target is open and therefore filled with the medium of propagation. Therefore the light is propagating through the medium.

Since the target plate is shiny (like a mirror) it reflects the pulse back onto the primary housing. The target could be metal, dielectric, or other material. This beam directly illuminates a detector. The detector could be a single pixel, but could also be multiple pixels. A filter can be used in front of the detector to suppress any background light that is not of the wavelength of interest.

The detector is connected to timing electronics to measure the amount of time it took for the pulse to travel from the source to the target and back.

This time is compared to the time measured during calibration at the factory in air. The difference in time from the air measurement to the measurement in the medium can be used to calculate the index of refraction.

Averaging of hundreds or thousands of measurements within a few seconds can reduce individual measurement errors or temporary disturbances (particulates, etc). Additional intelligence can be included that discard outliers, as the index should not change by a large percentage quickly (temperature, pressure, and salinity will change on the order of a few seconds, not sub-second). The exact algorithm for calculating the time is not described herein, as there are numerous algorithms for optimizing pulse detection. Any of these algorithms could be applied herein with the same intent and purpose.

The light source should be transparent for the medium of interest. For water, this is primarily the visible spectrum, while for blood this would be red or near-infrared. The light source can be modulated CW or pulsed. Pulsed has the advantage of freezing time and uses less power (diodes). CW light sources are generally cheaper and can employ any number of waveforms, chirps, or codes that are know in the radar and ladar fields to optimize range precision over a quasi-cw time period. No specific waveform is specified herein, but their use to measure range is within the scope of this disclosure. The example wavelengths of radiation used here are visible and infrared, however any wavelength of electromagnetic or acoustic energy are considered part of this disclosure.

The detector should be able to detect the wavelength of interest. For green/blue/red this would be silicon, but could be any other detector sensitive to visible light. For the infrared this would most likely be InGaAs, but could be any other detector sensitive to infrared light.

It is noted that if the primary sensor is a time of flight sensor (like a ladar), the primary sensor can be used in this same manner to calculated the index of refraction. However the target should be moveable so the sensor can be used to measure other objects of interest. This could be accomplished (for instance) by having a robotic arm fully extended and pointing the ladar at a calibrated point on the arm. This method is not the preferred embodiment as it is not a continuous measurement and will take more time to perform.

Integrated Index Measurement with Primary Sensor—Edge Detection. Another embodiment comprises an integrated solution where the refractometer is combined with the primary measurement sensor. Therefore both devices are in the same housing and view the medium through the same window. The measurement light source could be shared between the primary sensor and the index sensor, or be separate sources. They should be of the same wavelength, however, to ensure the most accurate measurements.

The index beam is angled such that it experiences total internal reflection (TIR) at the boundary of the window and the medium. The light that experiences TIR is directed or focused onto a detector array. The amount of light that totally internally reflects (and the location of the light on the detector) is affected by the index of the medium. By analyzing the amount or location of the TIR light on the detector, the index can be calculated using several standard methods currently used in industry.

Integrated Index Measurement with Primary Sensor—Holographic. Another embodiment comprises an integrated solution where the refractometer is combined with the primary measurement sensor. Therefore both devices are in the same housing and view the medium through the same window. The measurement light source could be shared between the primary sensor and the index sensor, or be separate sources. They should be of the same wavelength, however, to ensure the most accurate measurements.

In this embodiment, the holographic measurement technique described above is used to make the actual index measurements. A local oscillator (LO) beam is therefore split before the index measurement beam leaves the window, transmits through the medium, reflects off the target, enters the sensor, combines with the LO, and makes an interference pattern on the sensor. The spacing of the fringes on the interference pattern will define the angle of the incoming beam and therefore measure the index of the medium.

Indirect Index Estimation. This embodiment comprises estimating the refractive index of the medium as opposed to direct measurement. This can be performed by measuring other parameters of the medium (such as temperature, pressure, pH, and salinity) and then estimating the index of refraction based on tables or mathematical models for the primary sensor wavelength. This is not as accurate and does not take organic and inorganic particles in the medium into account. However, this is better than using a single refractive index for all medium conditions.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Described herein are devices and methods for making extremely accurate measurements in a medium by continuously measuring the index of refraction of the medium such as water or biological tissue. The index of refraction is the ratio of the speed of light in a vacuum to the speed of light in the medium. This is an important parameter as the index of refraction not only changes the time it takes for the light to travel through the medium, but also can change the angle of propagation. This is highly important when making very precise optical measurements in a medium that has a variable index of refraction. For instance, when taking a 3D laser scan of a scene at the bottom of the ocean, the correct index at that depth and temperature are needed in order to measure range and angle accurately and thus create a dimensionally correct 3D image. Described herein is a device for constantly measuring the index of refraction, and using the index of refraction data to constantly calibrate the optical measurement device. Preferably, a light source of the same wavelength as the primary measurement device is utilized. The light propagates through the medium at a know angle to a reflective surface (target) at a known distance. A sensor images the light spot on the target and calculates the centroid of the beam. This centroid is compared to the centroid measured in air or other calibrated index. The change in centroid location is used to calculate the index of refraction of the medium extremely precisely. The index is then used by the measurement device to correct for angle, time, or other offsets caused by the index of the medium. In addition, a primary measurement device (a ladar) that is optimized for data collection in a volume backscattering medium such as water or biological tissue is described. A number of these embodiments were demonstrated with a prototype instrument in the lab and results are included herein.

Figure 1:
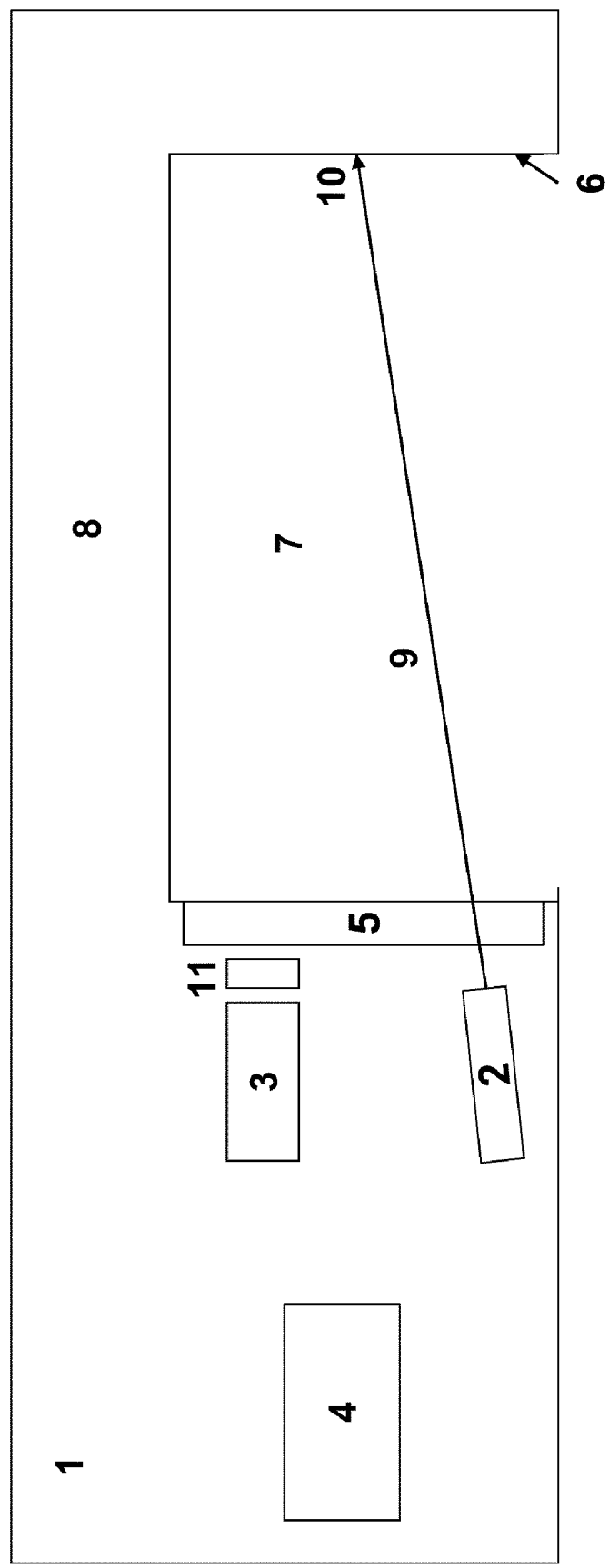
FIG. 1 is the side view of a preferred embodiment of an index measurement device. In this embodiment the camera images the spot on the target surface. The light rays should change angle as they cross from one material (index) to another. This is not done in the drawings for simplicity.

Index Measurement—Centroid. A preferred embodiment of an index measurement device is depicted in FIG. 1. This embodiment includes methods and devices that produce continuous, precise measurements of the index of refraction of the medium.

This preferred embodiment comprises a small, self contained underwater housing 1. The light source 2, detector 3, and electronics 4 are all in one part of the housing and view the outside environment through a window 5. This is called the primary part of the housing. A diffuse plate 6 that is in integral part of the housing is located a distance (for instance 10 cm) from the window. This is called the target portion of the housing. A light source 2 located in the primary part of the housing illuminates the target portion of the housing. The 10 cm distance from the primary window to the target is open and therefore filled with the medium of propagation 7. Therefore the light is propagating through this medium. The primary part of the housing 1 is connected to diffuse plate 6 by a very rigid structure 8. In the preferred embodiment the diffuse plate 6 is flat, but could be curved, wavy, striped, or any other complex 3D shape or with any complex pattern.

The light source 2 is rigidly positioned at an angle, so the light 9 meets the surface of the target 6 at an angle, such as 45°. The light creates a diffuse spot on the target. A sensor 3 located in the primary housing 1 is used to image the illuminated spot on the diffuse target 10. A sensor refers to any detector capable of imaging the diffuse target, 2D or 1D. A filter 11 may be used in front of the detector to suppress any background light that is not of the wavelength of interest.

Note that since the angle of source 2 is critical, the mounting of source 2 to camera 3 is particularly important, so mounting material coefficients of thermal expansion (CTEs) must be matched or controlled.

Figure 2:
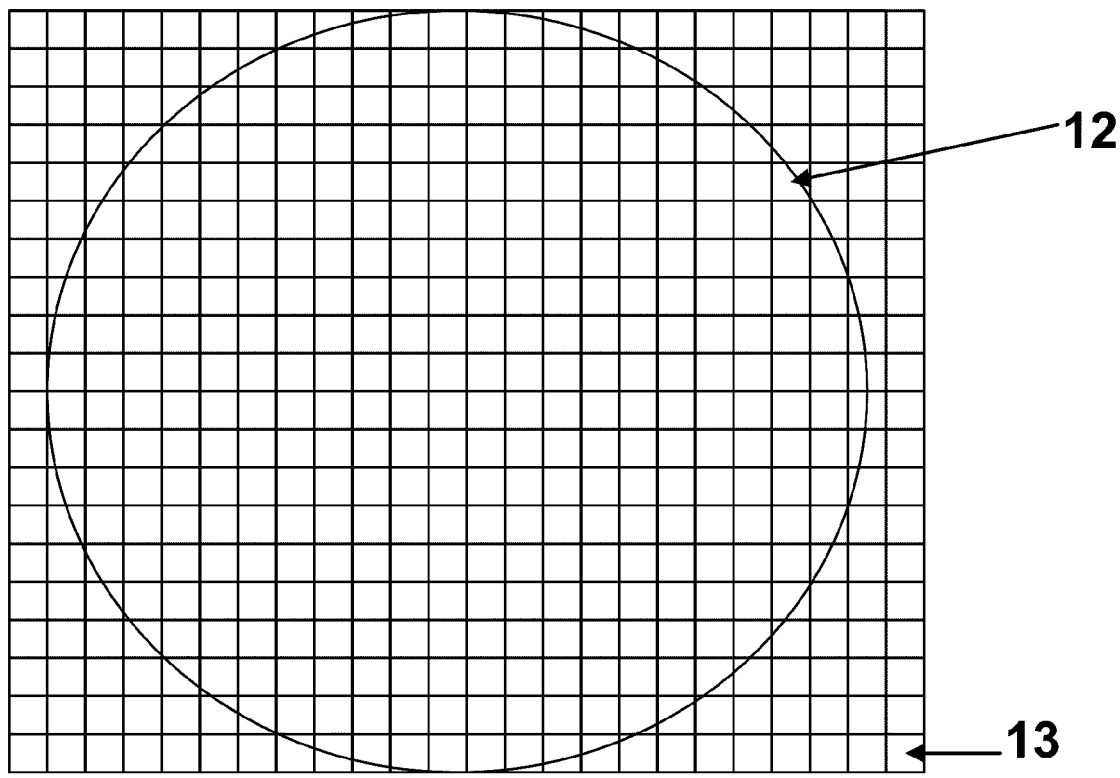
FIG. 2 is a drawing of the images spot on a 2D detector.

FIG. 2 shows an important aspect where the image of the illuminated spot 12 covers hundreds, thousands, or tens of thousands of detector elements 13. The image of the illuminated spot is analyzed in signal processing software to calculate the centroid of the spot. By having the spot imaged on a large number of pixels, sub-pixel resolution is achieved for the centroid. It is this sub-pixel resolution that allows for very precise measurement of the index of refraction.

This measured centroid is compared to the centroid location measured during factory calibration in air (when 7 is air). The difference in spot location from the air measurement to the measurement in the medium is used to calculate the index of refraction.

Averaging of hundreds or thousands of images within a few seconds can reduce individual image errors or temporary disturbances (particulates, etc). Additional intelligence can be included that discard outliers, as the index should not change by a large percentage quickly (temperature, pressure, and salinity will change on the order of a few seconds, not sub-second). The exact algorithm for calculating the centroid is not described herein, as there are numerous algorithms for centroid detection, such as highest intensity, quadratic curve fitting, two-dimensional quadratic interpolation, illumination center, modified illumination center, and least-squares methods such as principal component or eigenvector fits. Any of these algorithms could be applied herein with the same intent and purpose.

Figure 3:
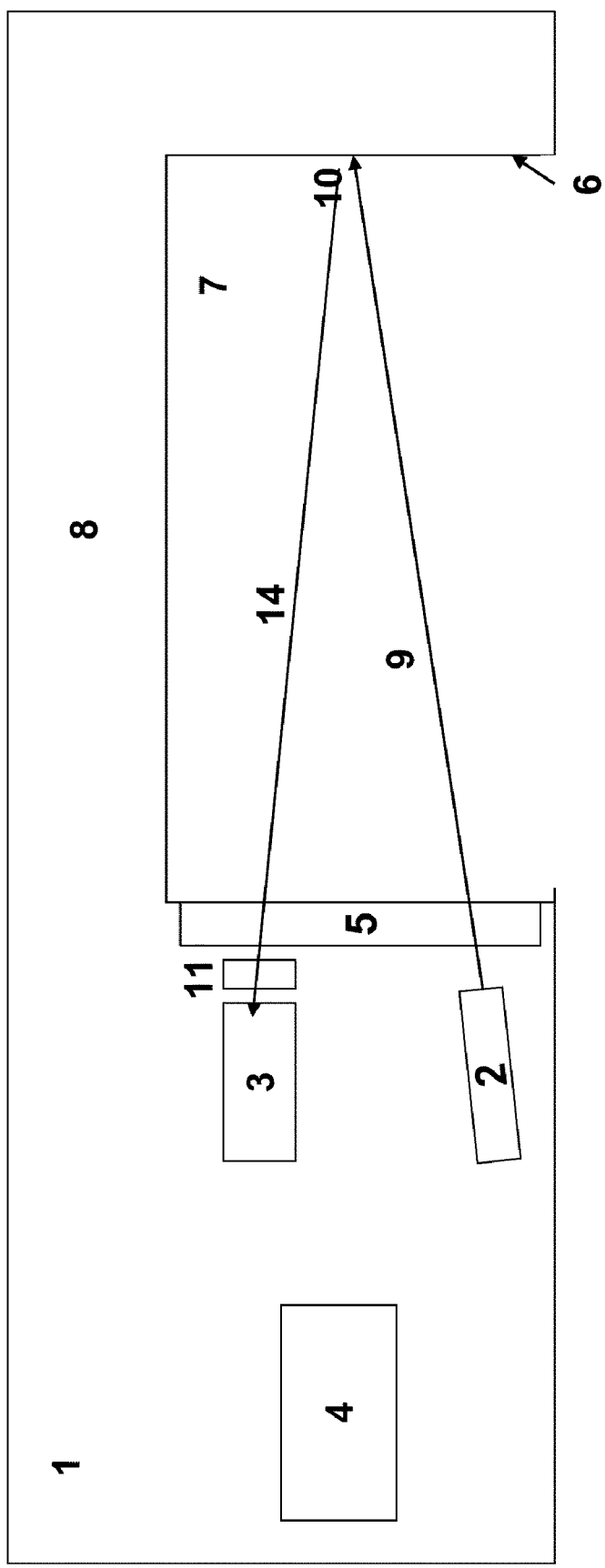
FIG. 3 is the side view of another embodiment of an index measurement device. In this embodiment the spot is reflected off the target surface and directly illuminates the detector. The light rays should change angle as they cross from one material (index) to another. This is not done in the drawings for simplicity.

FIG. 3 shows another embodiment, where the target plate 6 is shiny (like a mirror) and reflects the beam 14 back onto the primary housing window 5. This beam directly illuminates the detector (camera) 3. The centroid is then calculated as in the primary embodiment. The target 6 could be metal, dielectric, or other material. The mirror could be exposed directly to the medium 7, or reside behind a protective window.

Figure 4:
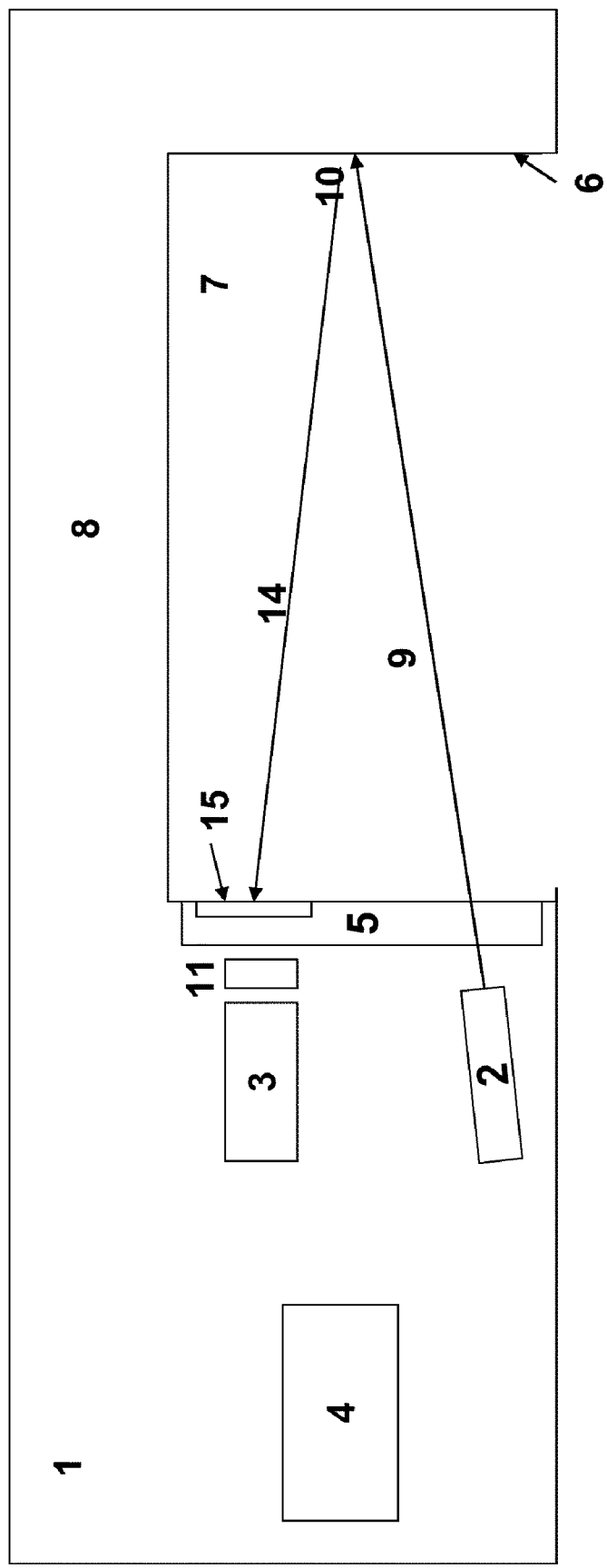
FIG. 4 is the side view of another embodiment of an index measurement device. In this embodiment the spot is reflected off the target surface and illuminates a diffuse surface on the main window. The camera images this diffuse surface to find the spot centroid. The light rays should change angle as they cross from one material (index) to another. This is not done in the drawings for simplicity.

FIG. 4 shows another embodiment, where the target plate 6 is shiny (like a mirror) and reflects the beam back onto the primary housing window 5. A diffuse window 15 is placed in front of the detector (camera) 3. The camera images this diffuse image of the beam. The centroid is then calculated as in the primary embodiment. The target 6 could be metal, dielectric, or other material. The mirror could be exposed directly to the medium, or reside behind a protective window.

The light source 2 should be transparent for the medium of interest. For water, this is primarily the visible spectrum, while for blood this would be red or near-infrared. The light source could be a laser, LED, OLED, collected incandescent bulb with a colored glass for wavelength selection, or any other directional or non-directional source. The light source can be CW or pulsed. Pulsed has the advantage of freezing time, whereas CW has the advantage of spatial averaging over a longer integration period. CW light sources are generally cheaper (for lasers), whereas pulsed sources use less power (for LEDs). The example wavelengths of radiation used here are visible and infrared, however any wavelength of electromagnetic or acoustic energy are considered part of this disclosure.

The detector 3 should be able to detect the wavelength of interest. For green/blue/red this would be silicon, but could be any other detector sensitive to visible light. For the infrared this would most likely be InGaAs, but could be any other detector sensitive to infrared light.

Figure 5:
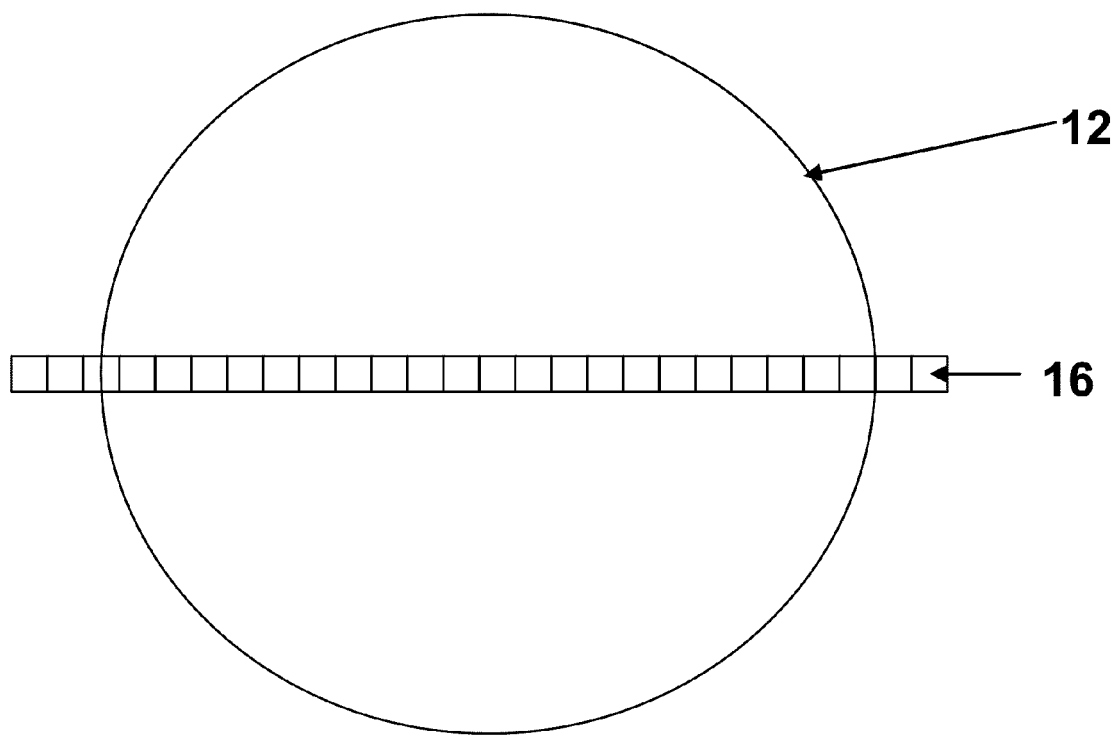
FIG. 5 shows the use of a 1D array to detect the centroid of an image of the spot in one dimension.

The preferred detector format is a 2D array such as a camera, however a 1D array could also be used. FIG. 5 shows the use of a 1D array to detect the centroid of an image of the spot 12 in one dimension. Again hundreds of detector elements 16 are used to acquire sub-pixel resolution.

Figure 6:
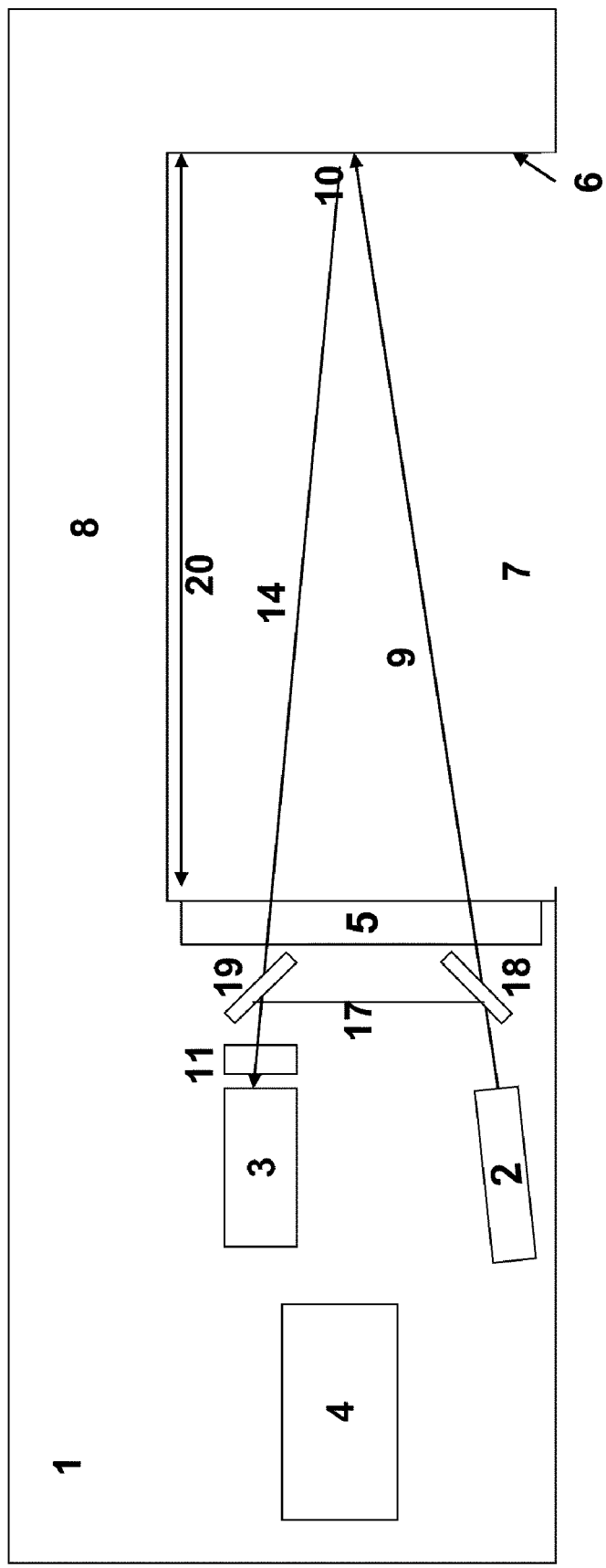
FIG. 6 is the side view of another embodiment of an index measurement device. In this embodiment the spot is reflected off the target surface and directly illuminates the detector. A local oscillator is used to create an interference pattern on the detector. The frequency of the interference pattern is used to detect the angle of incidence and therefore the index of refraction. The light rays should change angle as they cross from one material (index) to another. This is not done in the drawings for simplicity.

Index Measurement—Holographic. Another preferred embodiment is depicted in FIG. 6. This embodiment includes methods and devices that also produce continuous, precise measurements of the index of refraction of the medium.

This embodiment comprises holographic based measurements. Again, this embodiment comprises a small, self contained underwater housing 1. The light source 2, detector 3, and electronics 4 are all in one part of the housing and view the outside environment through a window 5. This is called the primary part of the housing. A shiny plate 6 that is in integral part of the housing is located a short distance (for instance 1 cm) from the window. This is called the target portion of the housing. A coherent light source 2 located in the primary part of the housing 1 illuminates the target portion of the housing 6. The 1 cm distance from the primary window to the target is open and therefore filled with the medium of propagation 7. Therefore the light 9 is propagating through the medium 7.

The coherent light source is rigidly positioned at an angle, so the light meets the surface of the target at an angle, such as 45°. Since the target plate is shiny (like a mirror) it reflects the beam 14 back onto primary housing window 5. The target 6 could be metal, dielectric, or other material. This beam directly illuminates the detector 3.

Figure 7:
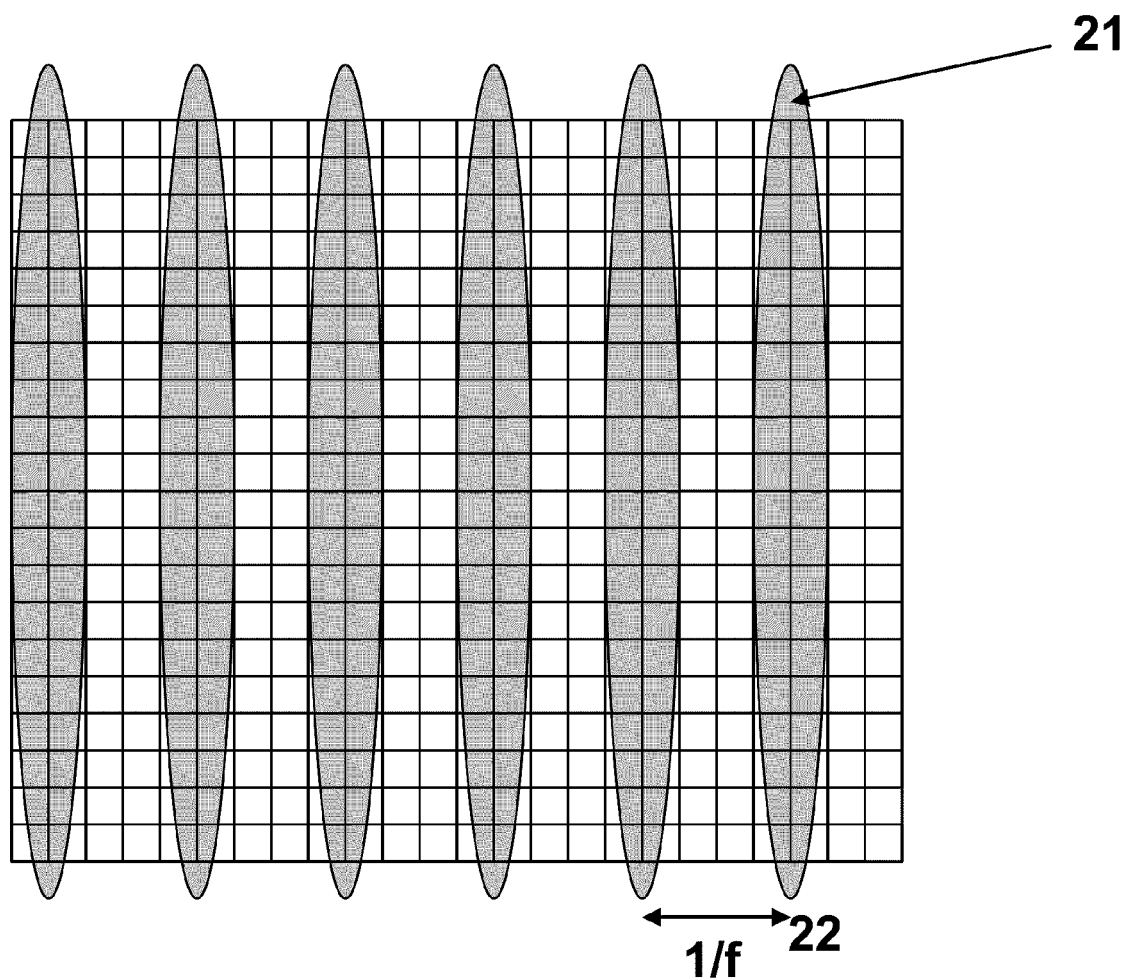
FIG. 7 is a drawing of the interference pattern on a 2D detector.

A portion of the outgoing beam is used as a local oscillator 17 to also illuminate the camera 3. Typically a beam splitter 18 is used to split off a portion of the beam. This beam splitter could be freespace or fiber based, depending on source 2. This local oscillator is combined with the return signal via another freespace or fiber beam splitter/combiner 19. The interference of this local oscillator with the return beam produces an interference pattern on the camera 3. An example interference pattern 21 is shown in FIG. 7. The spatial frequency 22 of this interference pattern is directly related to the angular difference of the two beams. By measuring this spatial frequency 22 on the camera image, the angle between the two beams can be measured with immense accuracy.

This angle is compared to the angle measured during calibration at the factory in air. The difference in angle from the air measurement to the measurement in the medium can be used to calculate the index of refraction.

Camera 3 can refer to any detector, 2D or 1D, capable of capturing the interference pattern. A filter 11 may be used in front of the detector to suppress any background light that is not of the wavelength of interest.

Averaging of hundreds or thousands of images within a few seconds can reduce individual image errors or temporary disturbances (particulates, etc). Additional intelligence can be included that discards outliers, as the index should not change by a large percentage quickly (temperature, pressure, and salinity will change on the order of a few seconds, not sub-second). The exact algorithm for calculating the spatial frequency of the interference pattern is not described herein, as there are numerous algorithms for frequency calculation, such as counting zero crossings, phase unwrapping, or Fourier transforms (with or without zero-padding). Any of these algorithms could be applied herein with the same intent and purpose.

Since holography allows for extremely accurate measurement of angle, the propagation distance 20 does not have to be as large. Therefore this method may be better suited for biological sensing where the sensor may have to be inserted in living tissue or bloodstreams.

The light source 2 should be transparent for the medium of interest. For water, this is primarily in the visible spectrum, while for blood this would be red or near-infrared. The light source for holography must be at least partially coherent which makes a laser the preferred source, however any partially coherent source could be used. The light source can be CW or pulsed. Pulsed has the advantage of freezing time, whereas CW has the advantage of spatial averaging over a longer integration period. CW light sources are generally cheaper (lasers), whereas pulsed sources use less power (diodes). The example wavelengths of radiation used here are visible and infrared, however any wavelength of electromagnetic or acoustic energy are considered part of this disclosure.

The detector 3 should be able to detect the wavelength of interest. For green/blue/red this would be silicon, but could be any other detector sensitive to visible light. For the infrared this would most likely be InGaAs, but could be any other detector sensitive to infrared light.

Figure 8:
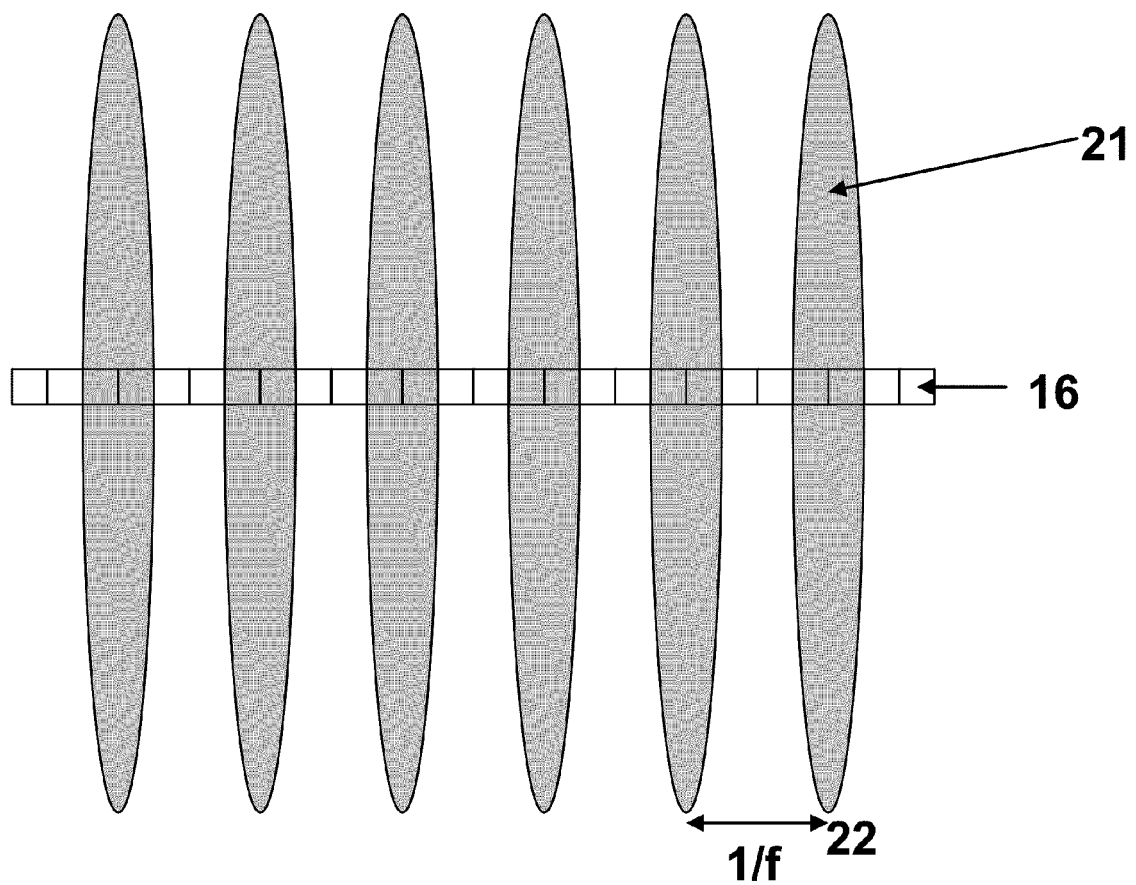
FIG. 8 shows the use of a 1D array to detect the spatial frequency of the interference pattern in one dimension.

The preferred detector format is a 2D array such as a camera, however a 1D array could also be used. FIG. 8 shows the use of a 1D array to detect the spatial frequency 22 of the interference pattern 21 in one dimension.

It should be noted that the principal of the holographic technique is that it measures the phase front of the incoming beam. In the spirit of this goal, any other phase front measurement device could be used as opposed to the camera and remain in the spirit of this disclosure. This can include a Schack-Hartmann wavefront sensor, or any other device capable of measuring the tip or tilt of the wavefront.

Figure 9:
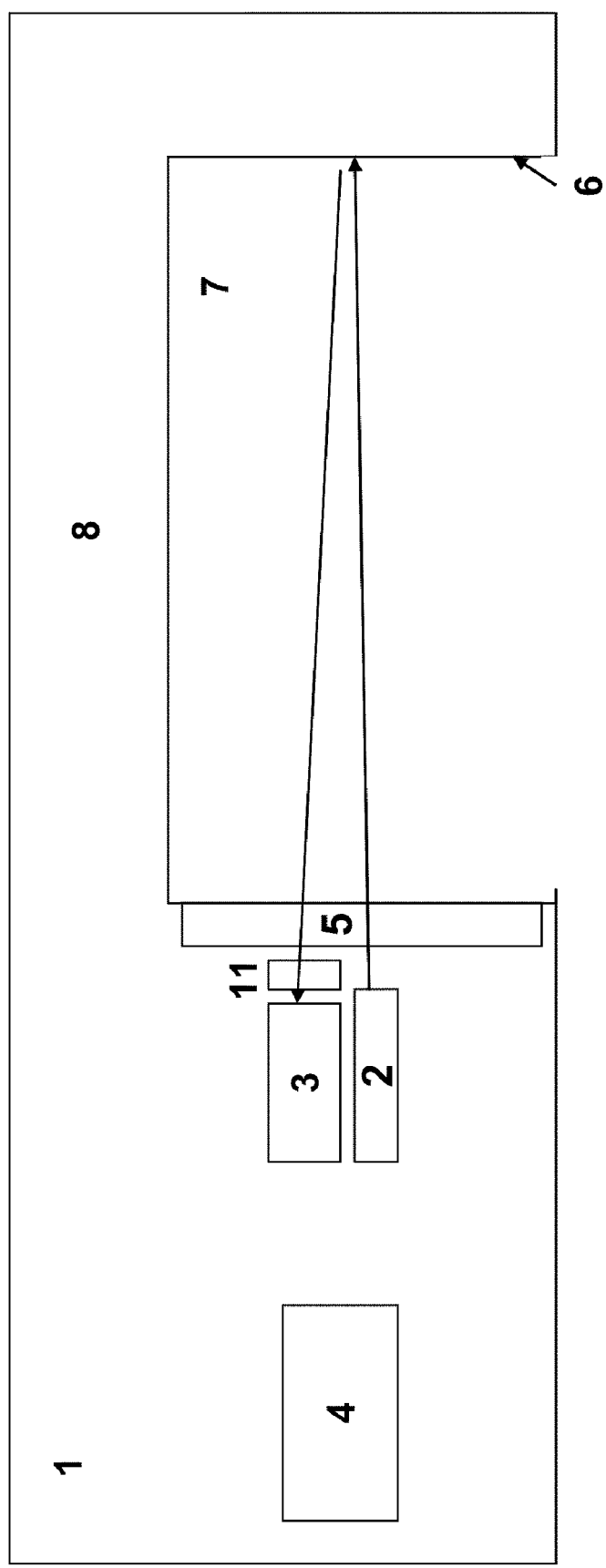
FIG. 9 is the side view of another embodiment of an index measurement device. In this embodiment a pulsed or coded waveform is reflected off the target surface and directly illuminates the detector. The time taken for the waveform to travel through the medium is used to calculate the index of refraction.

Index Measurement—Time. Another preferred embodiment is depicted in FIG. 9. This embodiment also produces continuous, precise measurements of the index of refraction of the medium.

This embodiment comprises time based measurements. Again, this embodiment comprises a small, self contained underwater housing 1. The light source 2, detector 3, and electronics 4 are all in one part of the housing and view the outside environment through a window 5. This is called the primary part of the housing. A shiny plate 6 that is in integral part of the housing is located a distance, 10 cm for example, from the window 5. This is called the target portion of the housing. A light source 2 located in the primary part of the housing sends a pulse or waveform of light to the target portion of the housing. The 10 cm distance from the primary window to the target is open and therefore filled with the medium of propagation 7. Therefore the light is propagating through the medium.

Since the target plate is shiny (like a mirror) it reflects the pulse back onto window 5. The mirror could be metal, dielectric, or other material. This beam directly illuminates detector 3. The detector could be a single pixel, but could also be multiple pixels. A filter 11 may be used in front of the detector to suppress any background light that is not of the wavelength of interest.

The detector is connected to timing electronics 4 to measure the amount of time it took for the pulse to travel from the source to the target and back.

This time is compared to the time measured during calibration at the factory in air. The difference in time from the air measurement to the measurement in the medium can be used to calculate the index of refraction.

Averaging of hundreds or thousands of measurements within a few seconds can reduce individual measurement errors or temporary disturbances (particulates, etc). Additional intelligence can be included that discards outliers, as the index should not change by a large percentage quickly (temperature, pressure, and salinity will change on the order of a few seconds, not sub-second). The exact algorithm for calculating the time is not described herein, as there are numerous algorithms for optimizing pulse detection. Any of these algorithms could be applied herein with the same intent and purpose.

The light source should be transparent for the medium of interest. For water, this is primarily the visible spectrum, while for blood this would be red or near-infrared. The light source can be modulated CW or pulsed. Pulsed has the advantage of freezing time and uses less power (diodes). CW light sources are generally cheaper and can employ any number of waveforms, chirps, or codes that are know in the radar and ladar fields to optimize range precision over a quasi-cw time period. Some of more popular techniques include AMCW phase detection, chirped AMCW, amplitude FMCW, true FMCW, and pulse modulation codes. No specific waveform is specified herein, but their use to measure range is within the scope of this disclosure. The example wavelengths of radiation used here are visible and infrared, however any wavelength of electromagnetic or acoustic energy are considered part of this disclosure.

The detector should be able to detect the wavelength of interest. For green/blue/red this would be silicon, but could be any other detector sensitive to visible light. For the infrared this would most likely be InGaAs, but could be any other detector sensitive to infrared light.

It is noted that if the primary sensor is a time of flight sensor (like a ladar), the primary sensor can be used in this same manner to calculated the index of refraction. However the target should be moveable so the sensor can be used to measure other objects of interest. This could be accomplished by having a robotic arm fully extended and pointing the ladar at a calibrated point on the arm. Another possibility is to have the scanner point at some other target that is at a known calibrated distance. This method is not the preferred embodiment as it is not a continuous measurement and will take more time to perform.

Coupled Index Measurement with Primary Sensor. Embodiments of this aspect include devices and methods for measuring the index of refraction of the medium, and sending those measurements to the primary sensor. The primary sensor then uses that index measurement to obtain highly accurate measurements in the medium.

Figure 10:
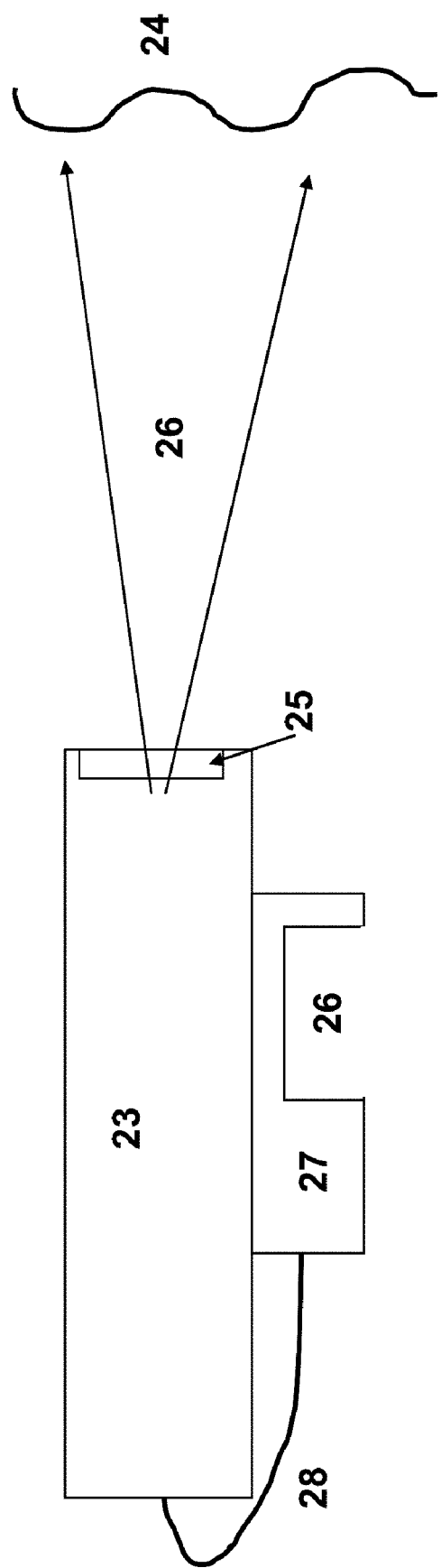
FIG. 10 is a drawing of an index measurement device coupled to a primary measurement device.

The preferred embodiment is shown in FIG. 10. The primary sensor 23 could be a 3D laser scanner, flash imager, triangulation imager, stereoscopic vision system, photometric stereo vision system, photoclinometry system, stereophotoclinometry system, or other optical measurement device to obtain highly accurate 3D data. The measurements of target 24 are made through window 25 in medium 26. This device is coupled with refractometer 27 that measures the index of medium 26 in real time at the same wavelength of the primary sensor 23. Refractometer 27 measures (continuously or discretely) the index of medium 26 and periodically updates primary sensor 23 with the index through data cable 28. Primary sensor 23 then uses the updated index as described in equations 1 and 2 to accurately measure range or angle. Other sensors (triangulation, photometric stereo, etc.) will not necessarily use the index as shown in equations 1 & 2, but the same corrections will be needed to make highly accurate measurements.

The term refractometer is used in general to represent any instrument capable of measuring the index of the medium at the primary sensor wavelength. This index correction is needed for making underwater measurements with accuracies better than a few inches.

Figure 11:
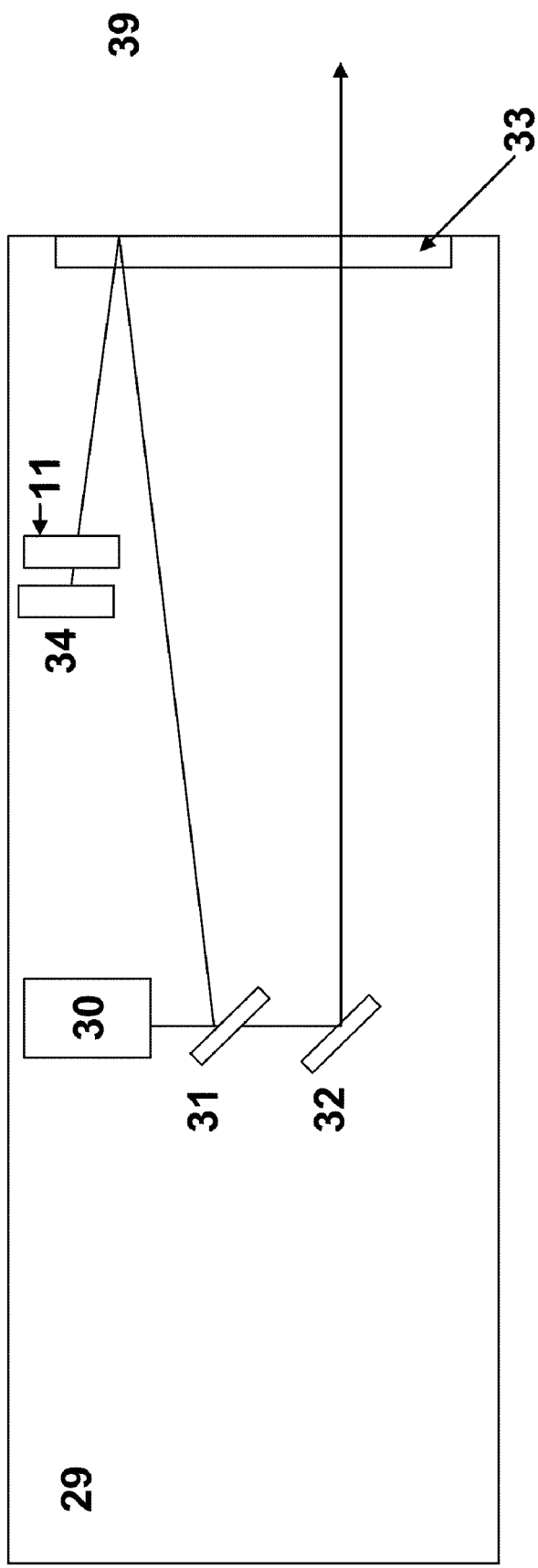
FIG. 11 is a drawing of an index measurement device integrated with the primary measurement device. In this embodiment, the index is measured with a beam that is split-off from the primary measurement beam, reflected off the window through total internal reflection, and measured on an independent detector array.

Integrated Index Measurement with Primary Sensor—Edge Detection. Embodiments of this aspect include devices and methods comprising integrated solutions where the refractometer is combined with the primary measurement sensor. FIG. 11 shows one such solution. A single housing 29 houses both the primary measurement device and the refractometer. In this embodiment a source 30 is used for both measurements, however different sources could be used. Part of the output beam is split off by a beamsplitter 31. The primary measurement beam is directed out of the sensor through window 33 by reflecting surface 32. Surface 32 could be a scanning mirror for a scanning device such as a scanning ladar. For an imaging sensor, surface 32 could be simply a mirror, or is optionally omitted if the measurement beam can exit the window without surface 32.

The index measurement beam is angled so it reflects off the outer surface of window 33 due to Total Internal Reflection (TIR). Window 33 could be a flat window, an angled window to assist in the TIR, or a prism that is separate from the window used by the measurement device. The amount of TIR will be dependent on the index of refraction of the measurement medium 39. The reflected beam is then directed (and possibly focused) on measurement sensor 34. A filter 11 could be used in front of the detector to suppress any background light that is not of the wavelength of interest. If sensor 34 is an array of detectors, it will detect a transition line from light to dark based upon the index of the medium. The location of this line on the sensor will determine the index of refraction as is known to one knowledgeable in the art.

Figure 12:
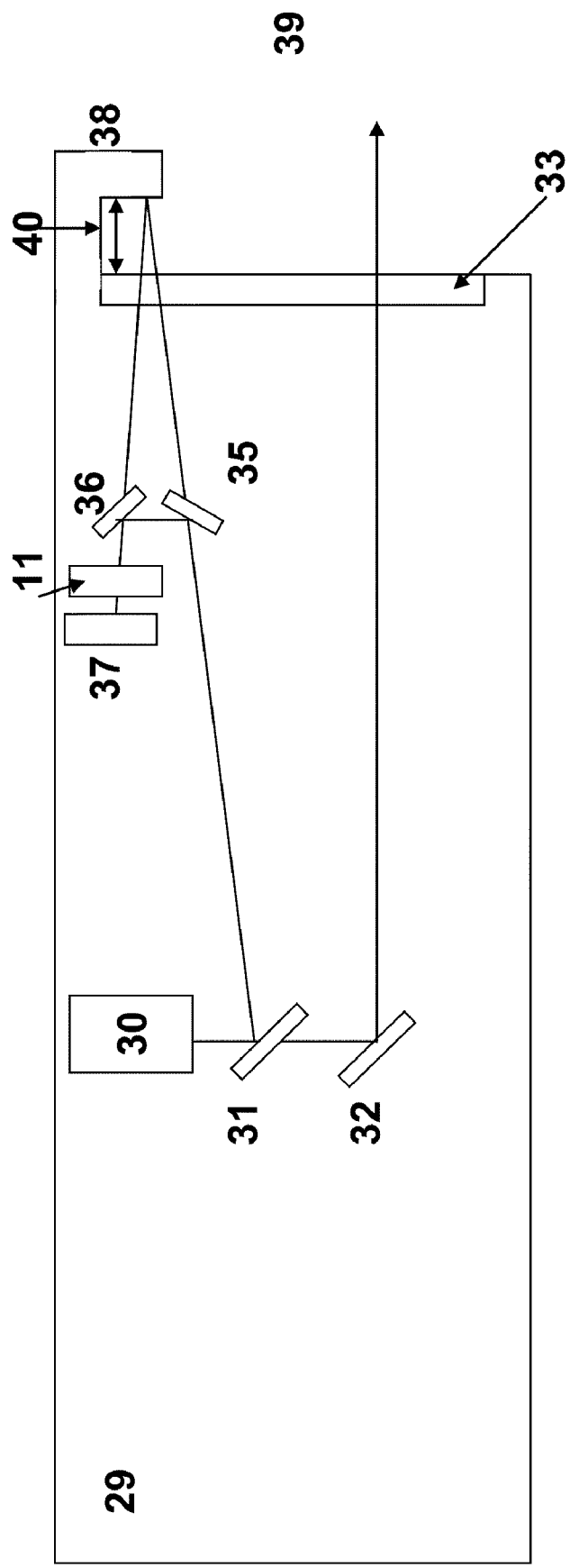
FIG. 12 is a drawing of an index measurement device integrated with the primary measurement device. In this embodiment, the index is measured with a beam that is split-off from the primary measurement beam, passes out a window and through the medium, reflected off a target, passes back into the sensor through the window, mixes with the LO, and creates an interference pattern on the sensor.

Integrated Index Measurement with Primary Sensor—Holographic. Embodiments of this aspect include devices and methods comprising integrated solutions where the refractometer is combined with the primary measurement sensor. These embodiments also produce continuous, precise measurements of the index of refraction of the medium. FIG. 12 shows such a solution. A single housing 29 houses both the primary measurement device and the refractometer. In this embodiment a coherent source 30 is used for both measurements, however different sources could be used. Part of the output beam is split off by a beamsplitter 31. The primary measurement beam is directed out of the sensor through window 33 by reflecting surface 32. Surface 32 could be a scanning mirror for a scanning device such as a scanning ladar. For an imaging sensor 32 could be simply a mirror, or is optionally omitted if the measurement beam can exit the window without surface 32.

A local oscillator (LO) is split from the index measurement beam by beam splitter 35. This beam splitter could be freespace or fiber based, depending on source 30. The rest of the beam exits through window 33, travels through medium 39, and reflects off target surface 38. Target surface 38 is an integral part of housing 29, extremely rigid, shiny enough to reflect the beam, and is only a short distance (a few centimeters for example) from window 33.

The coherent light source is rigidly positioned at an angle, so the light meets the surface of the target at an angle, such as 45°. Since the target plate is shiny (like a mirror) it reflects the beam back onto the window 33. The target 38 could be metal, dielectric, or other material. It could be exposed to medium 39, or be behind a protective window.

The beam returns through window 33, combines with the LO at beam combiner 36, and creates an interference pattern on sensor 37. Beam combiner 36 could be freespace or fiber based. An example interference pattern 21 is shown in FIG. 7. The spatial frequency 22 of this interference pattern is directly related to the angular difference of the two beams. By measuring this spatial frequency 22 on the camera image, the angle between the two beams can be measured with immense accuracy.

This angle is compared to the angle measured during calibration at the factory in air. The difference in angle from the air measurement to the measurement in the medium can be used to calculate the index of refraction.

Sensor 37 can refer to any detector, 2D or 1D, capable of capturing the interference pattern. A filter 11 could be used in front of the detector 37 to suppress any background light that is not of the wavelength of interest.

Averaging of hundreds or thousands of images within a few seconds can reduce individual image errors or temporary disturbances (particulates, etc). Additional intelligence can be included that discards outliers, as the index should not change by a large percentage quickly (temperature, pressure, and salinity will change on the order of a few seconds, not sub-second). The exact algorithm for calculating the spatial frequency of the interference pattern is not described herein, as there are numerous algorithms for frequency calculation, such as counting zero crossings, phase unwrapping, or Fourier transforms (with or without zero-padding). Any of these algorithms could be applied herein with the same intent and purpose.

Since holography allows for extremely accurate measurement of angle, the propagation distance 40 does not have to be as large. Therefore this method may be better suited for biological sensing where the sensor may have to be inserted in living tissue or bloodstreams.

The light source 30 should be transparent for the medium of interest. For water, this is primarily in the visible spectrum, while for blood this would be red or near-infrared. The light source for holography must be at least partially coherent which makes a laser the preferred source, however any partially coherent source could be used. The light source can be CW or pulsed. Pulsed has the advantage of freezing time, whereas CW has the advantage of spatial averaging over a longer integration period. CW light sources are generally cheaper (lasers), whereas pulsed sources use less power (diodes). The example wavelengths of radiation used here are visible and infrared, however any wavelength of electromagnetic or acoustic energy are considered part of this disclosure.

The detector 37 should be able to detect the wavelength of interest. For green/blue/red this would be silicon, but could be any other detector sensitive to visible light. For the infrared this would most likely be InGaAs, but could be any other detector sensitive to infrared light.

The preferred detector format is a 2D array such as a camera, however a 1D array could also be used. FIG. 8 shows the use of a 1D array to detect the spatial frequency 22 of the interference pattern 21 in one dimension.

It should be noted that the principal of the holographic technique is that it measures the phase front of the incoming beam. In the spirit of this goal, any other phase front measurement device could be used as opposed to the camera and remain in the spirit of this invention. This can include a Schack-Hartmann wavefront sensor, or any other device capable of measuring the tip or tilt of the wavefront.

Indirect Index Estimation. A method of this aspect comprises of estimating the refractive index of the medium as opposed to direct measurement. This can be performed by measuring other parameters of the medium (such as temperature, pressure, pH, and salinity) and then estimating the index of refraction based on tables or mathematical models for the primary sensor wavelength.

For instance, Austin and Halikas presented extensive tables and interpolation algorithms for the index of refraction of seawater as a function of wavelength of light, salinity, temperature, and pressure. The primary sensor typically uses a narrow band of energy, so the tables or models of only the primary sensor wavelengths band need be used. For seawater, a temperature sensor, pressure sensor, pH sensor, and salinity sensor (or any combination thereof) can be used to make measurements of the medium (seawater). These measurements are then either used as parameters in a mathematical model to calculate the index of refraction. An alternative is to use these measured values in a look-up table to find the index of refraction. There are 2 primary disadvantages of this method. First, by not making direct measurements the effects of organic and inorganic particles, or other chemicals in the water (oil, sulfur near vents, etc.) are not taken into account when calculating an index of refraction. A second disadvantage is the calculated refractive index now includes measurement errors from at least 3 different devices, whereas a direct measurement of index will only have a single measurement error. The example wavelengths of radiation used here are visible and infrared, however any wavelength of electromagnetic or acoustic energy are considered part of this disclosure.

Despite these obvious disadvantages, this method is better than assuming a constant refractive index for all medium conditions.

Figure 13:
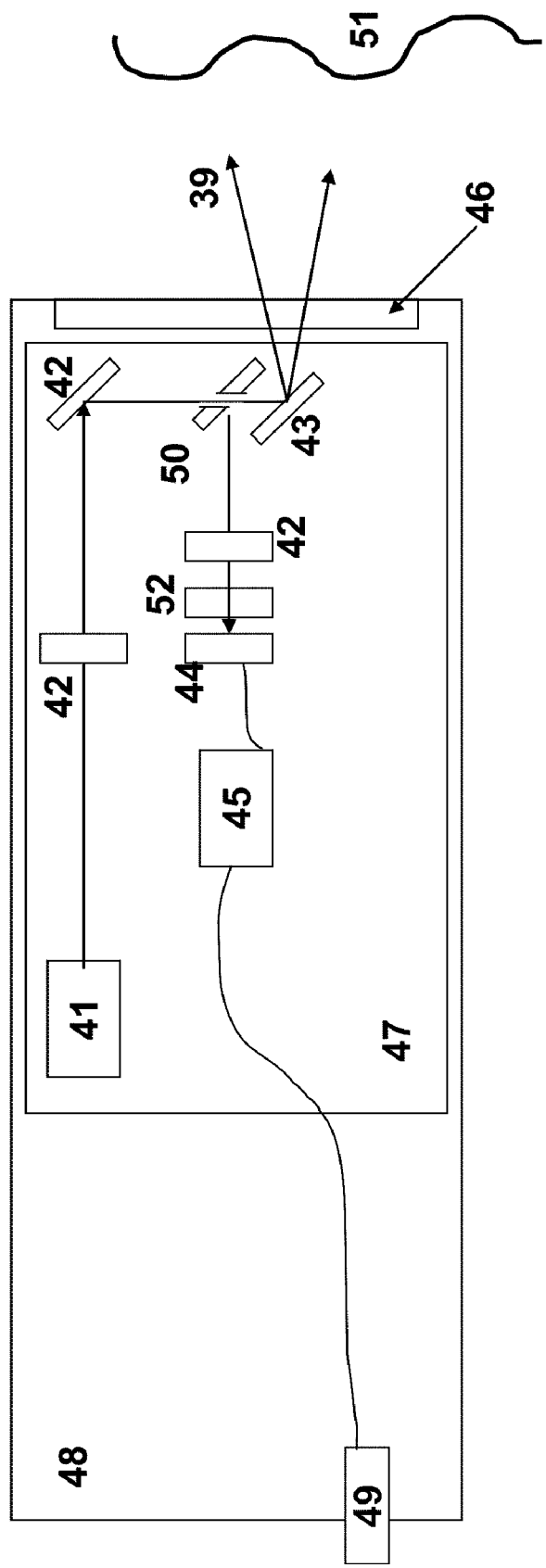
FIG. 13 is a drawing of a scanning ladar device optimized for data collection in a volume backscattering medium such as water or biological tissue.

Primary Measurement Sensor. In the above discussions, FIGS. 10-12 discuss the primary measurement sensor. Whereas the majority of the methods and devices describe herein are based on linking an index measurement device to a primary measurement device, this disclosure includes novel ideas for the primary measurement sensor to optimize it for measurements made in a backscattering medium such as water or biological tissue. One primary sensor of interest is a ladar. A basic ladar is shown in FIG. 13.

A ladar comprises a few basic elements: the source of energy 41, the optical train 42, a transmit/receive switch 50, the scanning device 43, the detector 44, electronics 45, and software.

The light source 41 should be transparent for the medium of interest. For water, this is primarily the visible spectrum, while for blood this would be red or near-infrared. The light source can be modulated CW or pulsed. Pulsed has the advantage of freezing time and uses less power (diodes). CW light sources are generally cheaper and can employ any number of waveforms, chirps, or codes that are know in the radar and ladar fields to optimize range precision over a quasi-cw time period. Some of more popular techniques include AMCW phase detection, chirped AMCW, amplitude FMCW, true FMCW, and pulse modulation codes. No specific waveform is specified herein, but their use to measure range is within the scope of this disclosure. The example wavelengths of radiation used here are visible and infrared, however any wavelength of electromagnetic or acoustic energy are considered part of this disclosure. Some examples of light sources include Light Emitting Diodes (LEDs), flash lamps, lasers, laser diodes, and solid state lasers. Any light source that can be used to produce range information is considered part of the disclosure, however the primary light sources of interest are lasers, diode lasers, and diode pumped solid state lasers.

The optical train 42 is a series of mirrors and lenses that are used to reshape the beam to its desired size and divergence, focusing the return light onto the detector, along with guiding the beams within the underwater housing 48. The housing keeps the components dry while submerged from shallow depths to several miles below the ocean surface. The housing can be purged and filled with dry gas to prevent condensation when the housing is cold (submerged in cold water). All the optical components are mounted on a rigid bench 47. The rigid bench could be made of any stiff material such as metal, graphite, or stone. The bench may or may not be rigidly attached to housing 48.

A scanning element 43 is used to direct the beam out of window 46 and scan across target 51. The scanning element can scan in either one dimension (a line scanner) or 2 dimensions. The laser radar calculates the range, thus giving the third dimension which allows for a 3D image to be created. The scanning element 43 can be mechanical or non-mechanical. Some examples of mechanical scanning include a galvanometer(s), spinning polygon mirror(s), piezo-electric, fast steering mirror, or even a micro-mechanical mirror (MEMS). Some examples of non-mechanical beam steering includes eletro-optic modulators, acousto-optic modulators, bubble based steerers, or liquid-crystal modulators. Any scanning mechanism (mechanical or non-mechanical) is considered part of this disclosure.

The detector 44 should be able to detect the wavelength of interest. For green/blue/red this would be silicon, but could be any other detector sensitive to visible light. For the infrared this would most likely be InGaAs, but could be any other detector sensitive to infrared light. Some example detectors include pn junctions, pin diodes, Avalanche PhotoDiodes (APDs), photo-multipliers tubes, bolometers, and MSMs. For underwater applications the primary wavelength is visible, so the primary detectors of interest include silicon pins, silicon APDs, and photomultiplier tubes, however any detector capable of detecting the return energy is considered part of this disclosure.

A filter 52 may be used in front of the detector 44 to suppress any background light that is not of the wavelength of interest. Some examples include bandpass filters, notch filters, etalons, and interference filters. Care must be taken with filter selection to ensure the primary wavelength of interest is not attenuated significantly by the filter.

Figure 14A:
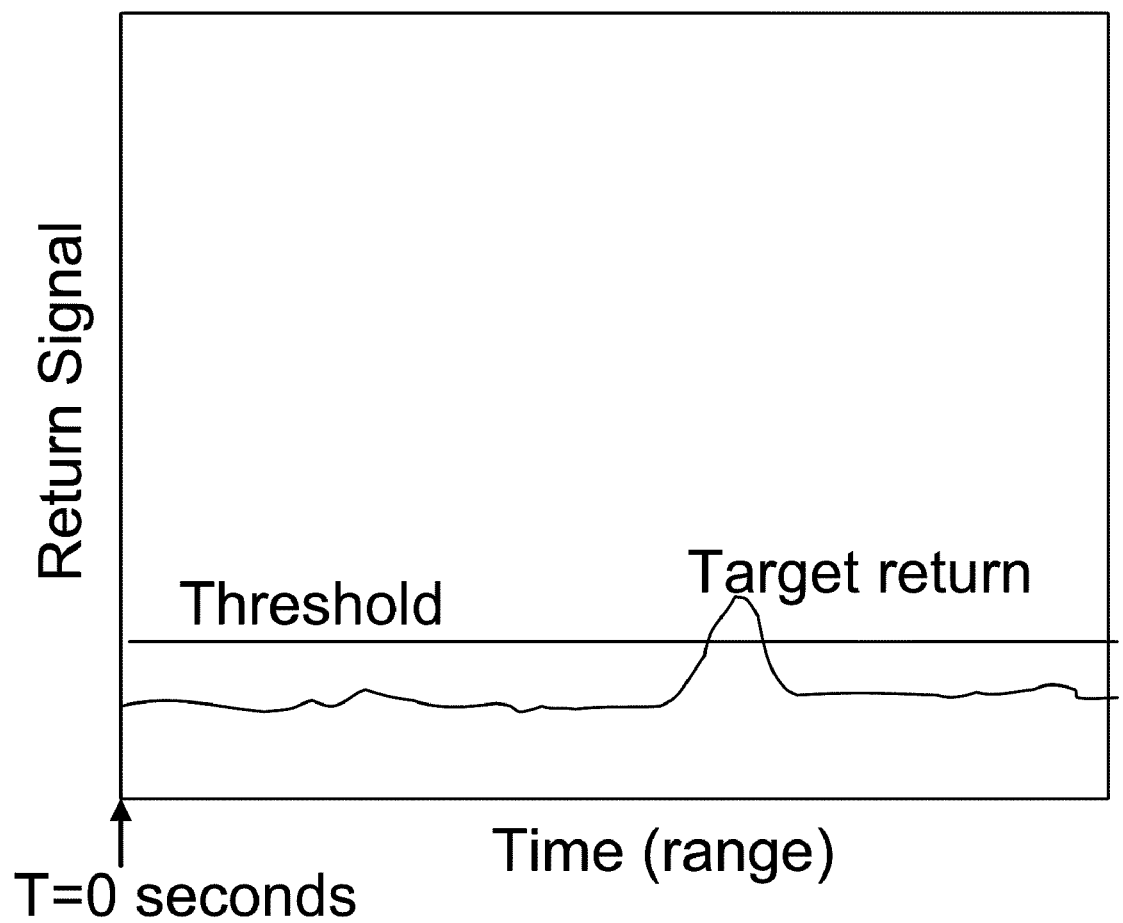
FIG. 14 is a drawing of the return signal from a pulsed ladar in air or vacuum (FIG. 14a) and a drawing of the return signal from a pulsed ladar in a volume scattering medium such as water or biological tissue (FIG. 14b).

The detector converts photons to electrons that are then processed by the electronics 45. The processing of the signal is one area where a ladar in a medium significantly varies from a ladar in air or a vacuum. Any ladar used in air (or vacuum) can simply send out a pulse of light, start a timer, and then wait until a signal comes back that crosses a threshold value as shown in FIG. 14*a*. The crossing of a threshold stops the timer, so the time of flight out and back to the target can be used to calculate range (as discussed in the Background Section). More complex methods can be used than threshold crossing, such as up and down-slope detection, differentiation, digitization, and constant fraction discrimination; however simple threshold crossing could be used.

Figure 14B:
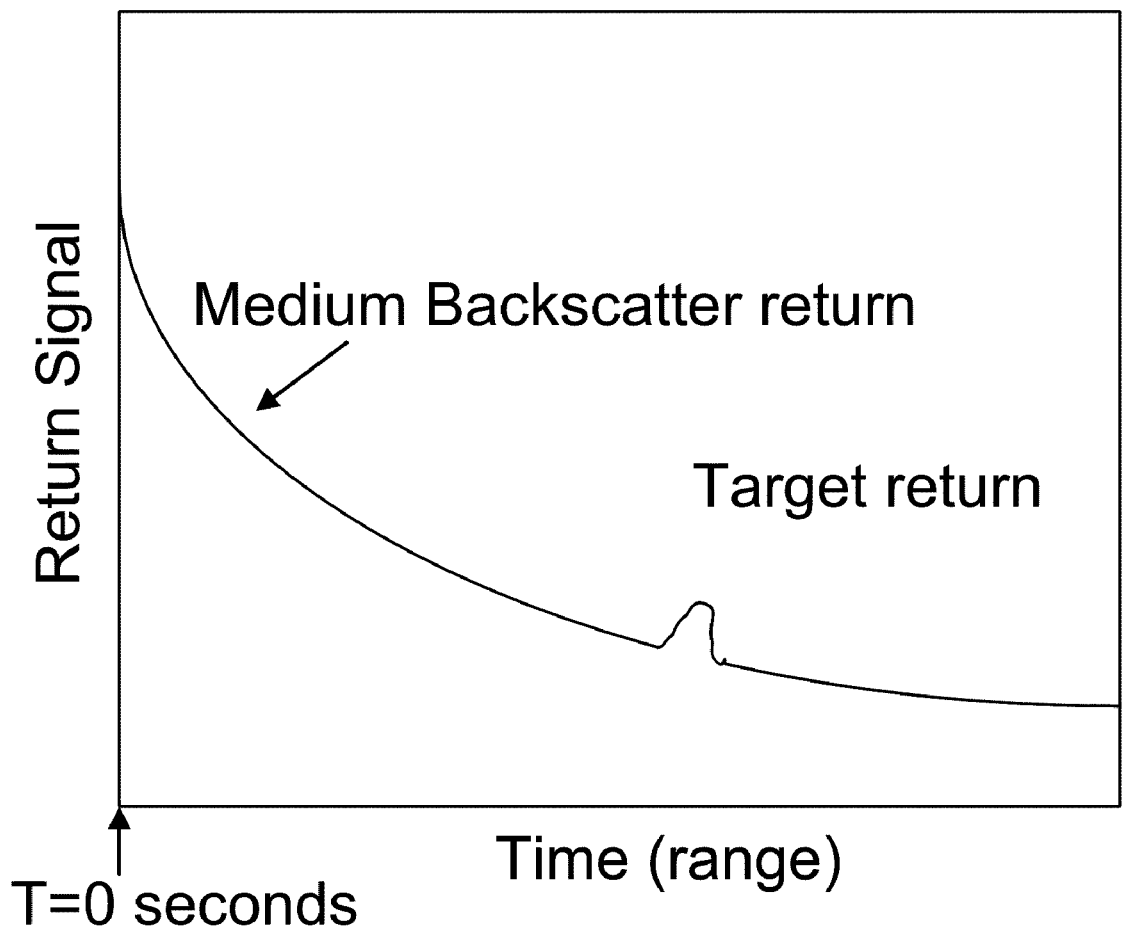

Most of these methods do not work in a volume scattering medium such as blood or water. The primary issue is the detector will see a return from time=0 seconds due to the backscatter from the medium as shown in FIG. 14*b*. Usually, this backscatter produces a higher signal on the detector than the return from the target, especially at shorter ranges. Therefore a threshold detection circuit will automatically trigger a detection as soon as the pulse leaves the housing and the true target is never seen.

One method to avoid this issue is to digitize the signal. Therefore the entire return signal can be seen from t=0 to max time or range as shown in FIG. 14*b*. Signal processing can then be performed to "remove" the signal due to the backscattering volume of the medium so the true target signal can be recovered. One novel method of achieving this is to fit a curve (usually a $1/R^2$) to the short range returns and then subtract that analytic curve from the entire signal. This will eliminate the backscatter volume signal and allow further filtering and processing to occur on the remaining signal to find the target range. Therefore in one embodiment, electronics 45 includes a pre-amplifier after the detector, a post amplifier, an analog filter, and then a digitizer. The signal processing calculates the backscatter curve from a first small sample of data (1-meter for instance). A curve is fit to this data and that curve is subtracted from the entire data return. With the backscatter volume now removed, the target range can be located by multiple methods, including simple peak detection after digital signal processing such as matched filtering.

The output of the electronics is sent to the outside world (ROV, boat, computer, etc.) via waterproof connectors 49 in housing 48.

Another novel way to reduce or remove the medium backscatter volume signal is through clever use of optical element 50 in FIG. 13. The transmit/receive (T/R) switch 50 is used in monostatic ladars to separate the transmit beam from the return signal. The system is considered monostatic since both the transmit and receive beams are co-aligned and can use the same small scanner 43. Examples of T/R switches include polarization based, holed mirrors, and obscuration based on an angled mirror. In FIG. 13, element 50 is shown as a holed mirror. In this embodiment, a mirror is used at ~45° with a small hole drilled through the center. The transmit beam passes through the center of the mirror, hits scanner 43, and illuminates target 51. Light scattered off both the medium and the target are captured by scanner 43 and directed back at element 50. Most of the return light is reflected off element 50 towards detector 44. A small amount of return light is lost through the central hole in the mirror. However at close ranges more of the light is lost through the central hole as opposed to light reflected from longer ranges. Therefore by appropriately sizing the central hole for the beam and target ranges of interest, the close range medium volume scattering can be minimized. This can reduce the amount of close range signal that reaches the detector (from the medium or a close range target), thus reducing the dynamic range required of the detector and electronics. It can also possibly eliminate the close range medium backscatter therefore eliminating the need for subtraction of the backscatter signal in post-processing. This novelty has not been located in the prior art.

The use of a polarizing beam splitter as the T/R switch does not attenuate the on-axis signal and therefore does not have the benefit of reducing the signal level from close range targets including the scattering medium. The obscuration/angled mirror approach achieves similar performance to the holed mirror by placing a small angled mirror in front of the receive optics, however this typically requires more mechanical components that must be kept in tight tolerance. The holed mirror has benefits over both other approaches.

Another possibility is to use a bi-static approach. In a bistatic ladar, the transmit and receive optical paths are separate up to the scanner. A bi-static system can be designed so the transmit beam and the receiver field of view do not overlap at close ranges, thereby reducing the dynamic range of the detector and electronics while also reducing the short range backscatter signal from the medium. This approach, however, typically requires the use of a much larger scanner since the transmit and receive fields-of-view are now side-by-side as opposed to co-aligned.

Therefore the clever use of a holed mirror for a monostatic ladar has advantages over other approaches by using a smaller scanner and less complicated optical system while reducing the detector and electronic dynamic range and reducing the close-range returns from the medium backscatter.

Note the scanning ladar is not limited to a single beam. Multiple beams can be scanned at the same time, thus increasing the effective data rate. Typically a multi-beam system uses a single laser source, a diffractive grating to split the single beam into multiple beams (1D or 2D array of beams) and then multiple detectors to receive light from the multiple points on the target. This approach typically requires multiple detectors, possibly multiple signal processors, and a higher power laser (a direct multiple of the number of beams). In the extreme case, the ladar becomes a "flash ladar" system where instead of scanning, a very large number of detectors are used (similar to a digital camera). The primary drawback with this approach is the cost of the 2D detector array, and the laser power required to receive a signal on the hundreds to tens of thousands of detectors simultaneously. All of these options are included in this disclosure as any of these options can take advantage of the novelties outlined above.

Note that all of the above embodiments could be applied in a general sense to any primary sensor needing to make an accurate measurement in any medium of interest. However, some embodiments are useful for making sub 6-inch precision optical 3D measurements in any type of water (fresh, brackish, or seawater) at any temperature, depth, or location in the world. Other embodiments are useful for making 3D measurements with a precision of 4-inches or less, for example, 2-inches or less.

Although the present invention has been described with reference to preferred embodiments, numerous modifications and variations can be made and still the result will come within the scope of the invention. Some of these include other known methods of angle or range measurements such as structured light for angular measurements or coded waveforms for time of flight measurements. No limitation with respect to the specific embodiments disclosed herein is intended or should be inferred.

The invention may be further understood by the following non-limiting examples.

EXAMPLE 1

Three Dimensional Mapping of Various Objects Under Water

Several of the devices and methods described herein have been realized and demonstrated underwater in the laboratory. A 30 foot×8 inch×8 inch tank was built in the lab that was capable of holding water. A 3 inch×3 inch window was fitted into one end of the tank to enable the laser system to see into the tank (water). This is analogous to a system working underwater as the housing will have a window separating the water environment from the air environment of the laser housing. Multiple targets were then placed in the tank at various ranges and underwater measurements were made in the lab. To extend the length of the tank, a mirror can be placed at the end of the tank to reflect the beam back down the tank towards a specular target. This bounces the beam back to the mirror and down the tank towards the sensor. This in effect doubles the length of the tank for specular targets.

The laser scanner realized in the lab can be described by FIG. 13. A pulsed green laser was used as the light source 41. Two 1-axis galvanometers are used as the scanning device 43 to enable two axis scanning. The galvanometers also allow for accurate pointing of the beam in both dimensions (azimuth and elevation) and pointing angle can be read from optical encoder outputs on each scanner. A silicon PiN was used as the detector 44, however a silicon APD or photo-multiplying tube could also be used. The detector package included a pre-amplifier. The electrical output of the detector/pre-amp was fed into electronics 45. The electronics included a post amplifier, analog filter, and an analog to digital converter (a digitizer). Therefore the entire analog signal is captured electrically and digitized.

One embodiment of the transmit/receive switch 50 was successfully implemented. A 4 mm hole was drilled in a gold mirror at a 45 degree angle. The mirror is then mounted at 45 degrees. The transmit beam passes through the hole in the mirror, bounces off the scanner, and illuminates the target. The return light is captured by the mirror and reflected towards the detector 44. This enables all the advantages previously mentioned above. This optical approach plus the selection of detector was extremely successful, as the output from the system was similar to FIG. 14a as opposed to 14b. This clearly verified and demonstrated a useful embodiment of the transmit/receive switch 50.

For the digitized signal, the peak of the return signal was identified, along with the time of the peak. This was compared to the start time (captured by a T=0 detector). The time difference was converted to range using equation (1), including the index of refraction of water correction (n). The index was calculated using the Indirect Index Estimation method described above.

The Indirect Index Estimation method was verified in the lab. An Atago PAL-R1 digital refractometer was purchased as a truth device. This device uses the Na line as the reference wavelength (589.3 nm). This refractometer was calibrated with distilled water, and then used to measure the index of refraction of the fresh tap water in the tank. The value output by the refractometer was 1.3323. This exactly matched the index of refraction table from Austin and Halikas [R. W. Austin and G. Halikas, "The index of refraction of seawater", SIO Ref 76-1 (Scripps Institution of Oceanography, La Jolla, Calif., 1976)] for the Na line at 26° C. (the temperature of the tank water). This provided a truth point for the table. The table was then used to determine the refractive index for the wavelength of the green laser (532 nm). This value is 1.33442.

Next, targets were placed in the water at various ranges up to the full 30 foot range of the tank. The distance to each target was measured from the window with a tape measure. Then, the laser sensor was used to measure the distance to the target at the various ranges. When the 1.33442 index value is used in equation 1, the range accuracy is <3 mm.

Specifically, a survey prism was placed at 15.335 m (50 foot measurement range using a mirror at the end of the tank). The range was measured with an accuracy of 1.5 mm using the Indirect Index Estimation method. If an average index value had been used (1.348), a 1% error (15 cm measurement error) would result! This verifies the need for the index correction devices and methods described herein.

In addition to single range measurements, the laser scanner was used to measure three-dimensional objects. For this capability, the laser is scanned in two dimensions using the galvanometers and range is measured at each point. Numerous objects were scanned at multiple locations and 3 dimensional datasets were collected and processed. Some examples of these datasets are shown in FIGS. 15-20.

Figure 15:
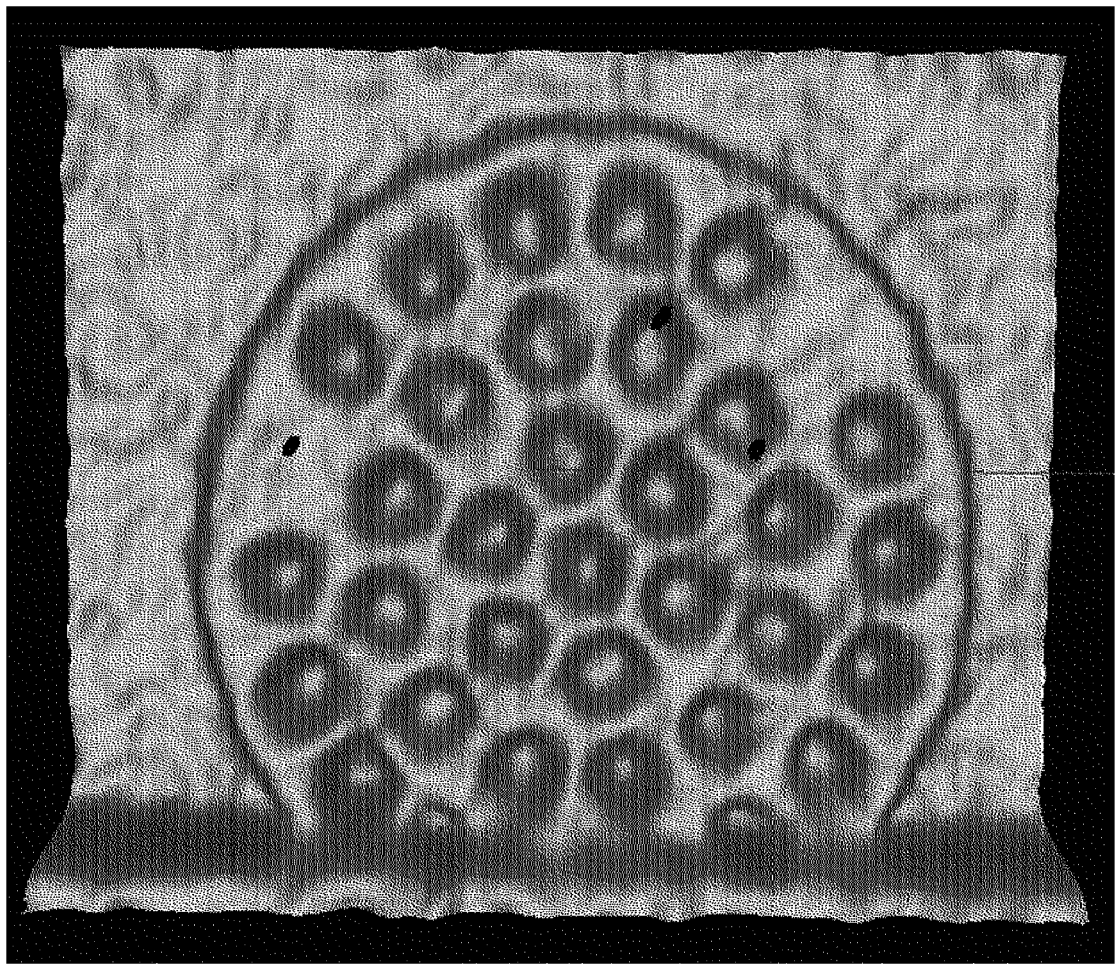
FIG. 15 shows actual data of a metal disk scanned at 20 foot range in water.

FIG. 15 shows a metal disk that was scanned at 20 foot range in water in front of a brick backstop. The holes are 9 mm in diameter and there is 4 mm of metal between the holes. This image clearly shows the angular resolution capability of the sensor.

Figure 16A:
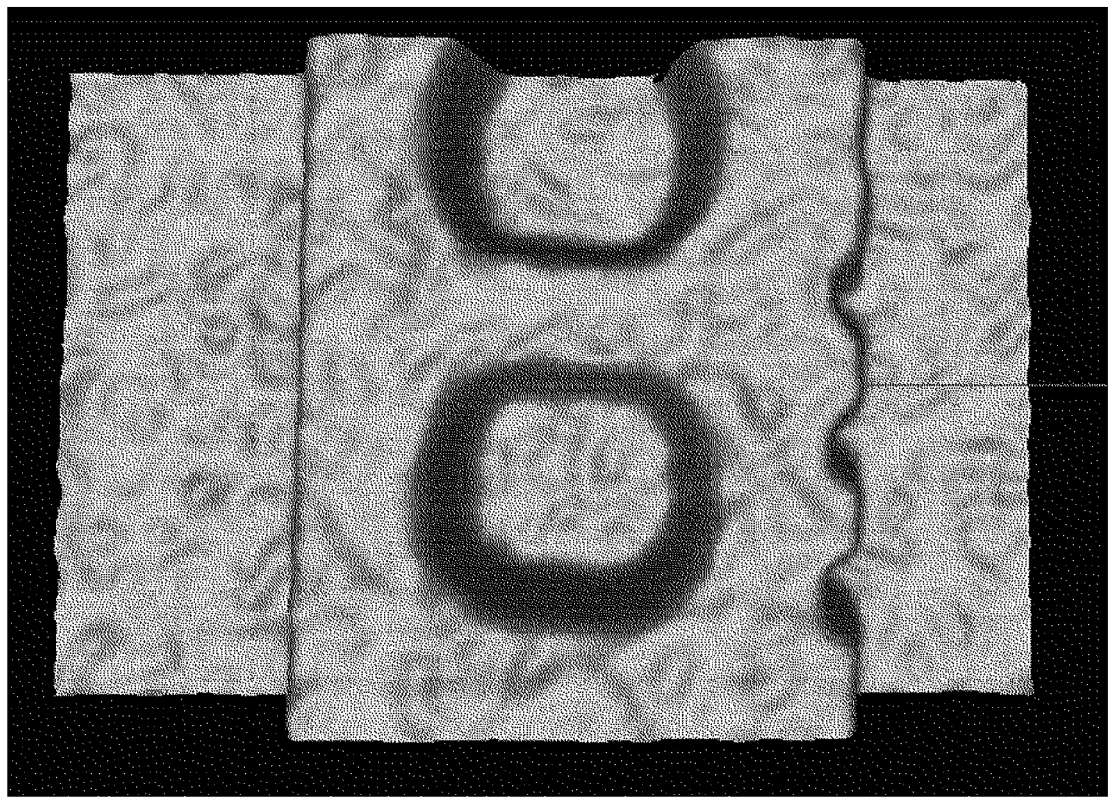
FIGS. 16A and 16B shows actual data of a brick scanned at 20 foot range in water.
Figure 16B:
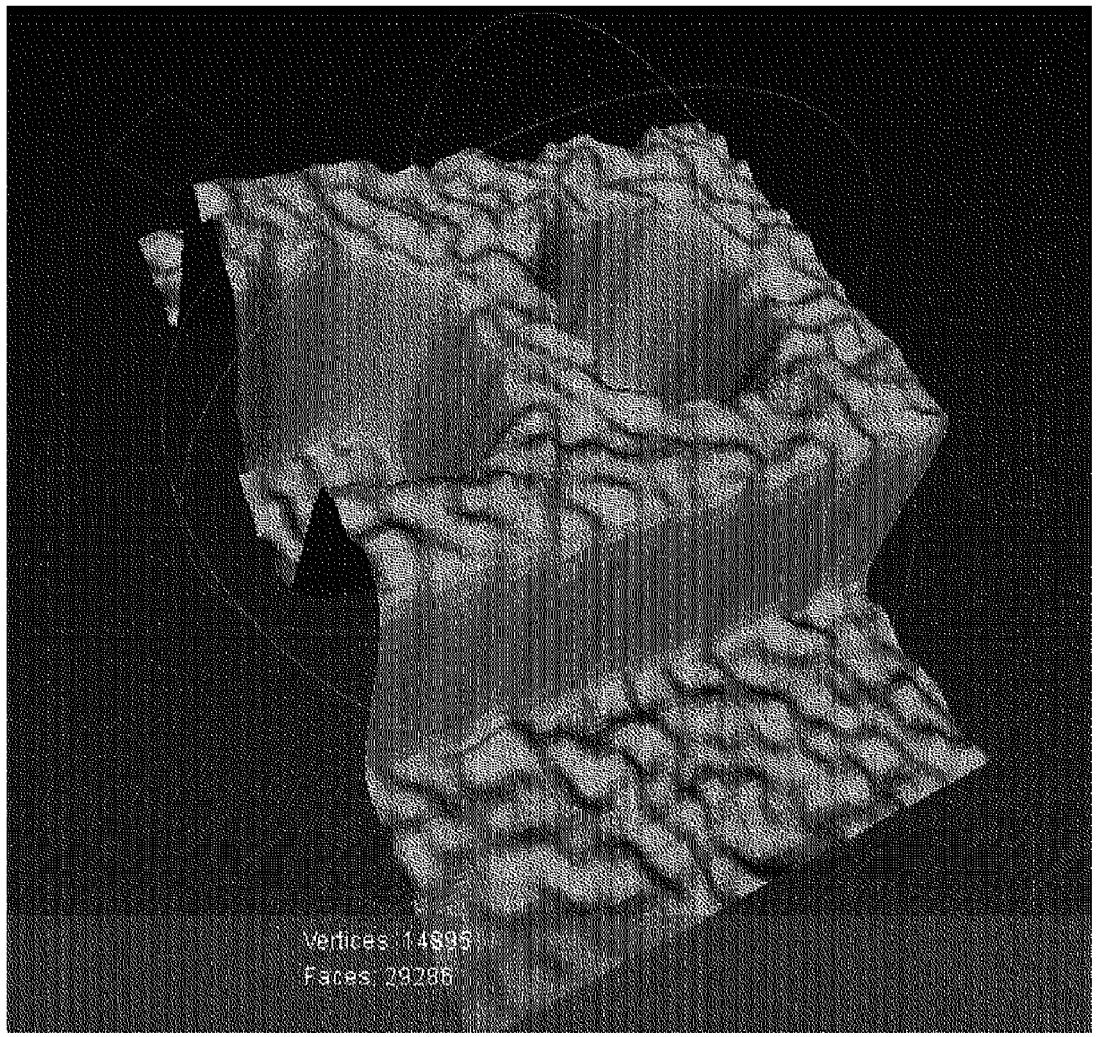

FIGS. 16A and 16B shows a brick scanned at 20 foot range in water in front of a brick backstop. The brick dimensions of 95 mm wide×55 mm thick×200 mm tall with a ridge 8 mm wide and holes 35 mm tall again show the angular and range resolution of the sensor.

Figure 17:
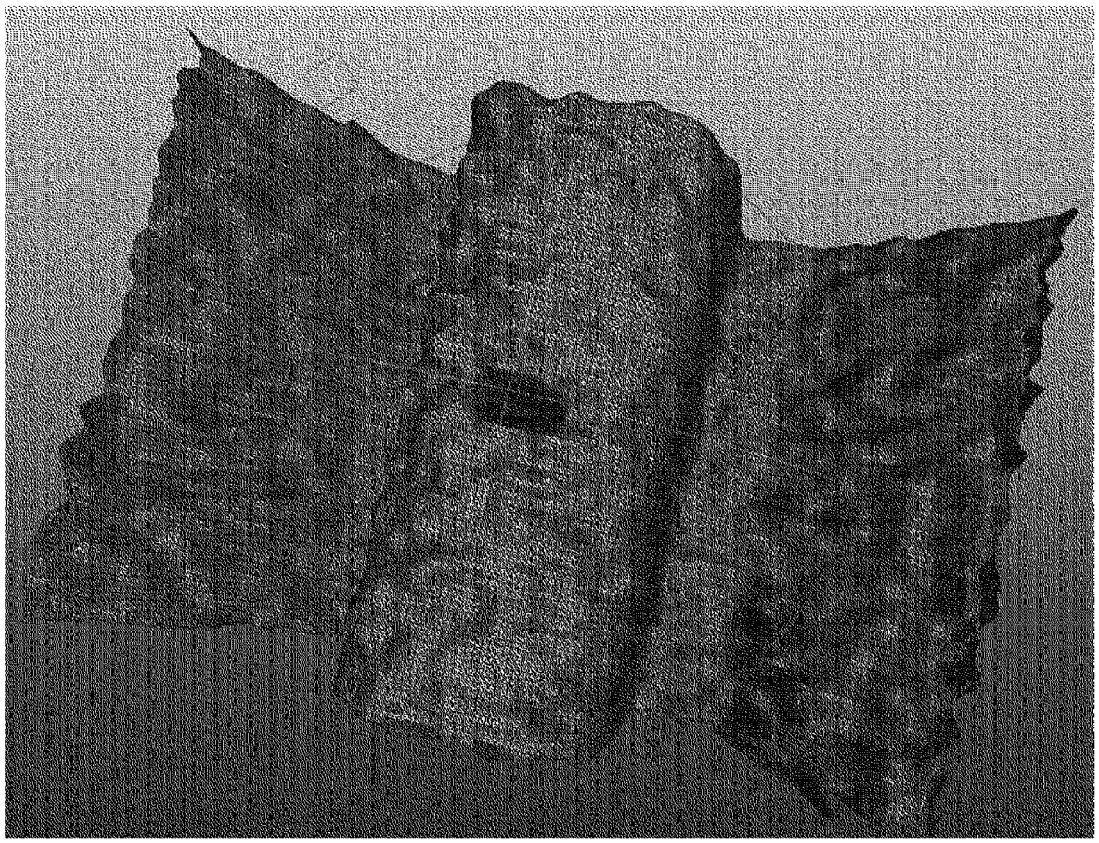
FIG. 17 shows actual data of a 6 cm PVC pipe scanned at 25 foot range in water.

FIG. 17 shows a 6 cm diameter PVC pipe scanned at 25 foot range in water in front of a tile backstop. There is a 2 mm hole in the pipe that is detected by the sensor at 25 foot range.

Figure 18A:
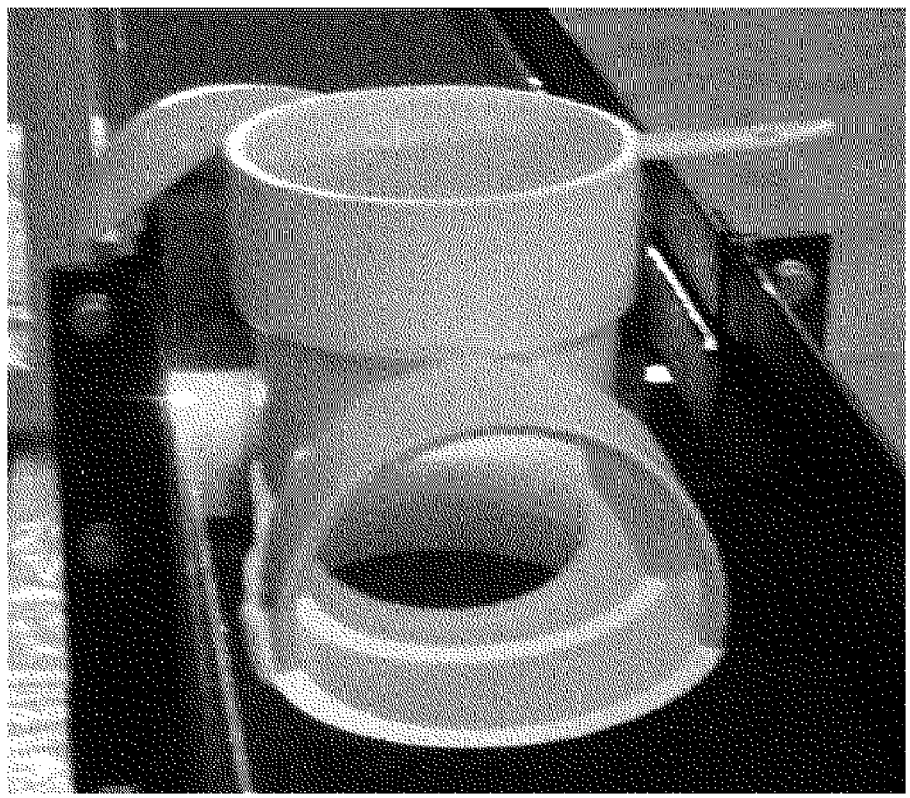
FIG. 18A shows a photograph of a 4 inch diameter PVC pipe.
Figure 18B:
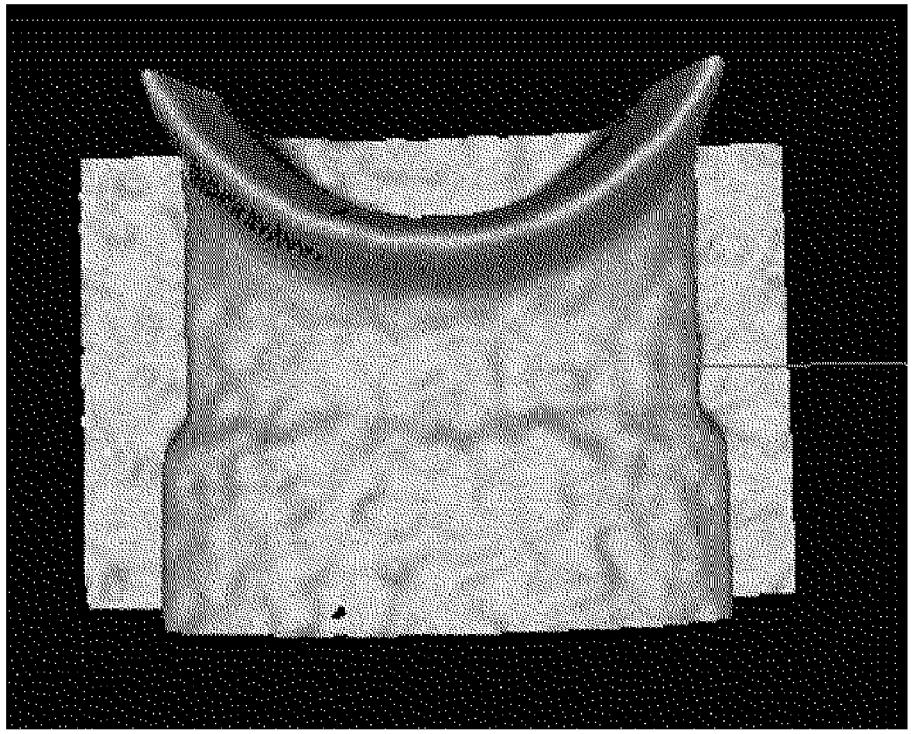
FIG. 18B shows actual data of the PVC pipe scanned in water at 20 foot range.

FIG. 18A shows a photograph of a 4 inch diameter PVC pipe. FIG. 18B shows the PVC pipe scanned in water at 20 foot range.

Figure 19:
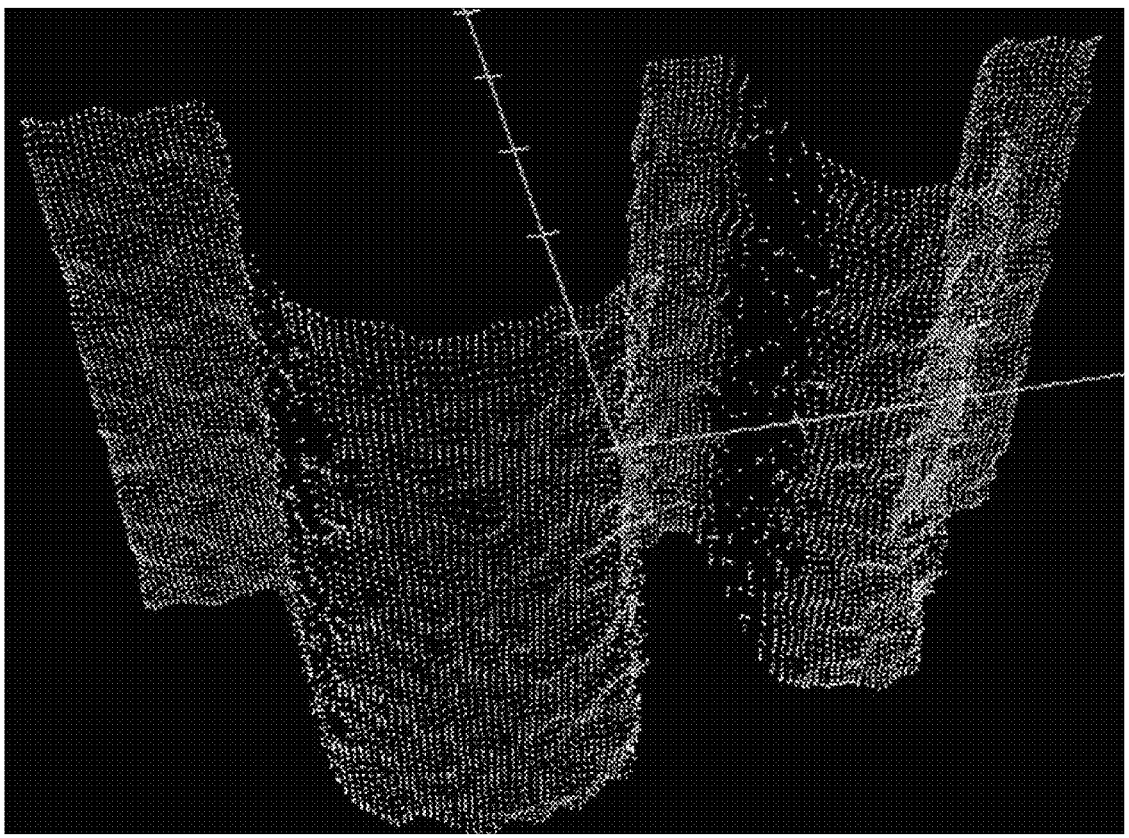
FIG. 19 shows actual data as a dot cloud representation of 32 mm diameter metal pipes scanned in water at 20 foot range.

FIG. 19 shows a dot cloud representation of 63 mm and 32 mm diameter metal pipes scanned in water at 20 foot range. The density of the data points across a 32 mm diameter pipe clearly shows how this technology provides much higher resolution than current sonar systems.

Figure 20:
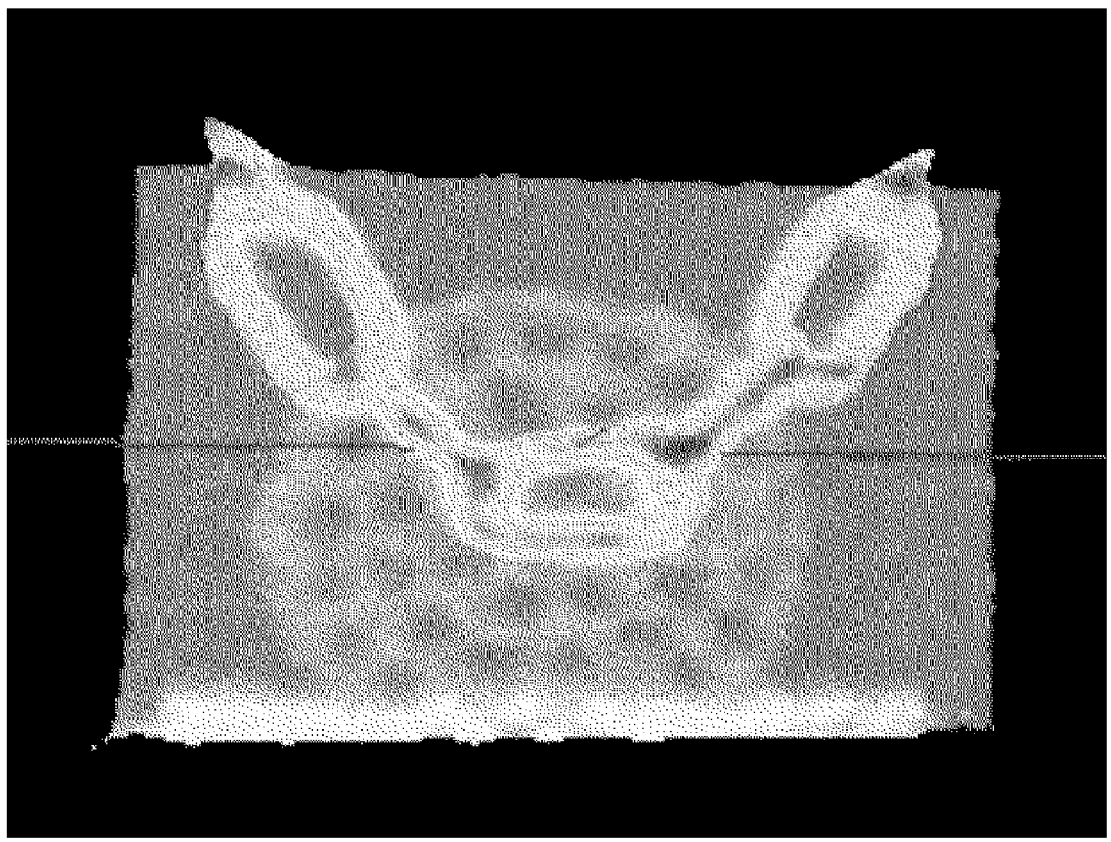
FIG. 20 shows actual data of a metal chain, positioned in front of the metal desk shown in FIG. 15, scanned in water at 20 foot range.

FIG. 20 shows a standard metal chain (1.75"×1" links, 0.25" thick), positioned in front of the metal disk of FIG. 15, scanned in water at 20 foot range.

This data and results described in this section clearly show the utility and validity of the devices and methods described herein for making extremely accurate underwater measurements with a laser system.

EXAMPLE 2

Useful Applications for Underwater 3D Imaging

The methods and devices described herein are useful for making highly accurate 3D measurements underwater. This technology can be used for several of the same applications that 3D laser scanners are used for terrestrially, plus additional applications that are unique to the underwater environment. For many of these applications the 3D scanner device is mounted on a moving platform (like a boat, Remote Operated Vehicle, or Autonomous Underwater Vehicle). For other applications it could be mounted on a tripod or other stable platform.

Some of these underwater applications include: pipeline inspection/survey, structure inspection, structural crack detection, pipe ovality inspection, cracks in pipe insulation, bubble detection, ice inspection, as-built inspection and measurement, weld inspection, anode inspection, chain inspection, and general inspection and measurement of any underwater structure. Just like terrestrial laser scanners, this metrology information can be used for safety inspection, environmental impact inspections, new construction, retro-fitting of old equipment, etc.

The technology described herein also enables a unique capability of the system to become an underwater total station. The same device can therefore be used as an extremely accurate survey tool. In this mode, the device is used to very accurately measure the range and bearing from one point in space to another (survey control points). This is very critical in deepwater construction and retro-fitting as often the distance and orientation between equipment (manifolds, wells, etc.) is not known. The current state of the art technology to measure these distances includes scaffolding that is brought to the surface and measured, complicated acoustic systems that take hours to measure, and electrical systems that require wires to be placed underwater. The use of this laser system will take only a few seconds to make the measurement and therefore is a clear benefit over the current state-of-the art. In addition, retroreflectors (prisms, mirrors, retroreflective tape or metal, etc.) can be used as the target to define the target point and to extend the operating distance.

EXAMPLE 3

Useful Example Embodiments

A typical embodiment is a primary measurement device that is coupled with an instrument that measures the index of refraction of the medium. The index of refraction measurements are used by the primary measurement device to correct for index changes and allow extremely accurate measurements. This is needed for time of flight and angular corrections. It is not only useful for time of flight measurements, but is also useful for angle based measurements. A few examples include ladar, scanning ladar, flash ladar, triangulation, stereoscopic vision, photoclinometry systems, stereo-photoclinometry systems, and photometric stereo. Note that all of the above embodiments could be applied in a general sense to any primary sensor needing to make an accurate measurement in any medium of interest. However, the preferred use is for making sub 6-inch or sub 4-inch precision optical 3D measurements in any type of water (fresh, brackish, or seawater) at any temperature, depth, or location in the world.

In another embodiment, the wavelength of light used to measure the index of refraction is the same wavelength used for the optical measurement device. It is known that the index of refraction of a medium varies by wavelength, so this allows for accurate and relevant index measurements. Other embodiments include:

Centroid method of index measurement device and methods.

Holographic method of index measurement device and methods.

Time method of index measurement device and methods.

Edge detection integrated with primary measurement sensor device and methods.

Holographic method integrated with primary measurement sensor device and methods.

Index estimation through inference, as opposed to direct measurement device and methods. This can be performed by measuring other parameters such as temperature, pressure, pH, and salinity and then estimating the index of refraction based on tables or mathematical models for the primary sensor wavelength. This is not as accurate and does not take organic and inorganic particles or other chemicals in the medium into account. However, this is better than using a single refractive index for all medium conditions.

An exemplary embodiment includes a monostatic ladar that uses a central obscuration to reduce the dynamic range of the detector and electronics along with the volume backscatter from the medium at short ranges. The central obscuration could be from a hole in the receive optic, or from an actual obscuration such as a secondary mirror. Providing these benefits while remaining monostatic allows a smaller aperture for the scanning device than needed for a bistatic system. The holed mirror is a more elegant approach as it typically requires fewer components than an actual central obscuration.

REFERENCES

R. W. Austin and G. Halikas, "The index of refraction of seawater", SIO Ref 76-1 (Scripps Institution of Oceanography, La Jolla, Calif., 1976).

U.S. Pat. Nos. 5,696,577; 5,446,529; 6,963,354; 5,231,401; 5,343,284; 5,457,639; 5,309,288; 5,617,201; 5,565,978; 7,030,976; 6,133,989; 6,414,746; 3,680,963; 4,640,615; 4,964,721.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A method of making range, angle, or imaging measurements in a medium, the method comprising the steps of:
    making a range, angle, or imaging measurement in a medium;
    measuring or calculating an index of refraction of the medium; and
    correcting the range, angle, or imaging measurement for errors associated with use of an approximate index of refraction different from the measured or calculated index of refraction of the medium.

2. The method of claim 1, wherein the range or imaging measurement is made by a method selected from the group consisting of: laser scanning, ladar, flash ladar, laser triangulation, photometric stereo, stereoscopic vision, structured light, photoclinometry, stereo-photoclinometry, holographic systems, AMCW phase detection, chirped AMCW, amplitude FMCW, true FMCW, pulse modulation codes, time of flight pulse detection, and any combination of these, and wherein the angle or imaging measurement is made by a device comprising elements selected from the group consisting of scanning systems, a multi-detector system or camera (2D or 3D) where each detector pixel equates to an angle, and any combination of these.

3. The method of claim 1, wherein the range or angle measurement and index of refraction measurement are made at locations within 20 meters of one another within the medium.

4. The method of claim 1, wherein the range, angle, or imaging measurement is an electromagnetic energy based measurement and wherein the measurement of the index of refraction of the medium is made at the wavelength of the electromagnetic energy measurement.

5. The method of claim 1, wherein the step of measuring or calculating an index of refraction of the medium comprises the steps of:
    passing a beam of electromagnetic, acoustic or laser energy from a first medium into the medium;
    determining a parameter of the beam of energy associated with the beam passing from the first medium into the medium; and
    relating the parameter of the beam of energy to the index of refraction of the second medium.

6. The method of claim 5, wherein the parameter of the beam of energy is selected from the group consisting of: an angular deflection of the beam, a spatial deflection of the beam over a known distance, a speed of the beam, a phase of the beam, a time required for the beam to traverse a known distance, a total internal reflection (TIR) angle for transmission of the beam from the first medium into the medium, an intensity change of the beam after TIR and any combination of these.

7. The method of claim 5, wherein the determining step includes measuring a deflection of the beam by measuring a first deflection of the beam when the medium is a reference medium and measuring a second deflection of the beam when the medium is the medium for which the index of refraction is to be measured.

8. The method of claim 5, wherein the determining step includes measuring a time required for the beam to traverse a known distance by measuring a first time required for the beam to traverse a known distance in the medium when the medium is a reference medium and measuring a second time required for the beam to traverse a known distance in the medium when the medium is the medium for which the index of refraction is to be measured.

9. The method of claim 5, wherein the determining step includes
measuring a total internal reflection (TIR) angle for transmission of the beam from the first medium into the medium by measuring a first total internal reflection angle for transmission of the beam from the first medium into the medium when the medium is a reference medium and measuring a second total internal reflection angle for transmission of the beam from the first medium into the medium when the medium is the medium for which the index of refraction is to be measured; and/or
measuring an intensity change of the beam upon TIR.

10. The method of claim 5, wherein the first medium is a window comprising a material selected from the group consisting of glass, plastic, crystal, polymer, acrylic, sapphire, and any combination of these.

11. The method of claim 5, wherein the first medium comprises a gas, air or dry nitrogen.

12. The method of claim 1, wherein the medium is the medium for which the index of refraction is to be measured and comprises water, fresh water, sea water, or biological tissue.

13. The method of claim 1, wherein the step of measuring or calculating an index of refraction of the medium comprises the steps of:
measuring a physical parameter of the medium selected from the group consisting of: a temperature of the medium, a pressure of the medium, a pH of the medium, a salinity of the medium and any combination of these; and
relating the physical parameter of the medium to the index of refraction of the medium, wherein the index of refraction is determined from the physical parameter(s) of the medium using a mathematical model, analytic function, look up table or interpolation between points in a look up table.

14. The method of claim 13, wherein the look-up table includes values of the index of refraction of the medium for a range of values of the physical parameter of the medium.

15. The method of claim 13, wherein the analytic function is a function of wavelength or the look-up table includes values of the index of refraction of the medium for a range of wavelength values; wherein one or more values corresponds to a wavelength utilized by a primary measurement sensor, and wherein the medium comprises water, fresh water, brackish water, seawater or biological tissue.

* * * * *